(12) United States Patent
Barbeau

(10) Patent No.: US 8,871,744 B2
(45) Date of Patent: Oct. 28, 2014

(54) COMPOUNDS AND METHODS FOR SELECTIVELY TARGETING TUMOR-ASSOCIATED MUCINS

(75) Inventor: Donald L. Barbeau, Evanston, IL (US)

(73) Assignee: B & G Partyers, LLC, Evanston, IL (US)

( * ) Notice: Subject to any disclaimer, the term of this patent is extended or adjusted under 35 U.S.C. 154(b) by 451 days.

(21) Appl. No.: 13/135,911

(22) Filed: Jul. 18, 2011

(65) Prior Publication Data
US 2012/0022016 A1    Jan. 26, 2012

Related U.S. Application Data

(60) Provisional application No. 61/399,996, filed on Jul. 21, 2010.

(51) Int. Cl.

| | | |
|---|---|---|
| *A01N 43/04* | (2006.01) | |
| *A61K 31/70* | (2006.01) | |
| *A61K 31/715* | (2006.01) | |
| *C08B 37/00* | (2006.01) | |
| *C07H 5/04* | (2006.01) | |
| *C07H 5/06* | (2006.01) | |
| *A61K 31/7056* | (2006.01) | |
| *A61K 31/7042* | (2006.01) | |
| *A61K 31/7004* | (2006.01) | |
| *A61K 31/7016* | (2006.01) | |
| *A61K 31/702* | (2006.01) | |
| *A61K 47/48* | (2006.01) | |
| *C07H 15/12* | (2006.01) | |
| *C07H 15/26* | (2006.01) | |

(52) U.S. Cl.
CPC ........... *A61K 31/715* (2013.01); *A61K 31/7056* (2013.01); *A61K 31/7042* (2013.01); *A61K 31/7004* (2013.01); *A61K 31/7016* (2013.01); *A61K 31/702* (2013.01); *A61K 47/48046* (2013.01); *A61K 47/48092* (2013.01); *A61K 47/4823* (2013.01); *C07H 15/12* (2013.01); *C07H 15/26* (2013.01)
USPC .................. 514/62; 514/23; 514/53; 514/54; 536/55; 536/55.1; 536/55.2

(58) Field of Classification Search
CPC ........... A61K 31/7042; A61K 31/7056; A61K 47/48092; C07H 15/26
USPC ........... 514/53, 54, 62, 23; 536/55, 55.1, 55.2
See application file for complete search history.

(56) References Cited

U.S. PATENT DOCUMENTS 7,119,079 B2 * 10/2006 Barbeau .......................... 514/54

FOREIGN PATENT DOCUMENTS

| WO | WO2004/026307 | 1/2004 |
|---|---|---|
| WO | WO2004/013135 | 12/2004 |
| WO | WO2009/022171 | 2/2009 |
| WO | WO2009/133070 | 5/2009 |

OTHER PUBLICATIONS

Derynck, R., Akhurst, F.J., Balmain, A. (2001) TGF-β signaling in tumor suppression and cancer progression. Nature Genetics, vol. 29, p. 117-129.*
Halder, S.K., Beauchamp, R.D., Datta, P.K. (2005) A Specific Inhibitor of TGF-β Receptor Kinase, SB-431542, as a Potent Antitumor Agent for Human Cancers. Neoplasia, vol. 7, p. 509-521.*
Ansel, H.C., Allen, Jr., L.V., Popovich, N.G. (1999) Pharmaceutical Dosage Forms and Drug Delivery Systems. Published by Lippincott Williams & Wilkins, p. 48-53.*
CAS Registry No. 301836-41-9. Entered into STN on Nov. 9, 2000.*
Yingling, Johnathon M. et al. Development of TGF-B Signaling Inhibitors for Cancer Therapy in Nature Reviews/Drug Therapy 3:1011 (2004).
Byfield, SD etal. "SB-505124 Is a Selective Inhibitor of Transforming Growth Factor-B Type I Receptors ALK4, ALK5 and ALK7" in Molecular Pharmacology 65:744-752 (2004).
Rausch, MP et al. "An orally Active Small Molecule TGF-B Receptor I Antagonist Inhibits the Growth of Metastatic Murine Breast Cancer" in Anticancer research 29:2099-2110 (2009).
Petersen, M et al. "Oral administration of GW788388, an inhibitor of TGF-B type I and II receptor kinases, decreases renal fibrosis" in Kidney International 73: 705-715 (2008).

* cited by examiner

*Primary Examiner* — Scarlett Goon

(57) ABSTRACT

The present invention relates to pharmaceutical compositions containing tumor-selective targeted inhibitor glycoconjugates. These bioconjugates are ALK5 inhibitors covalently bound to biocompatible carrier molecules which selectively target and specifically bind to Muc4 that is overexpressed on a variety of tumor cell types. The ALK5 inhibitors are conjugated to tumor targetable glycans through a covalent linker. Preferably the acid-labile linker is designed to be stable in plasma and releases pharmacologically active inhibitors through acid-catalyzed hydrolysis in the acidic environment of the target tumor where the inhibitor activity is restored. Because the glycoconjugates are stable at physiological pH and in plasma, they advantageously reduce undesirable systemic ALK5 inhibitor activity; however, the preferable glycoconjugates are acid-labile conjugates that can be hydrolyzed upon reaching the more acid environment of the tumor.

5 Claims, No Drawings

COMPOUNDS AND METHODS FOR SELECTIVELY TARGETING TUMOR-ASSOCIATED MUCINS

CROSS-REFERENCE TO RELATED APPLICATIONS

This patent application claims the benefit of prior filed provisional application No. 61/399,996 filed Jul. 21, 2010, titled Compounds and Methods for Targeting Tumor-Associated Mucins, which is hereby incorporated by reference in its entirety.

BACKGROUND OF THE INVENTION

The incidence of breast cancer in the United States in 2010 was 209,060, and the number of deaths was 40,230 (National Cancer Institute U.S. National Institutes of Health). Estrogen receptor negative breast cancer refers to a specific subtype of breast cancer that does not express the genes for estrogen or progesterone receptors. Triple-negative breast cancer refers to a specific subtype that does not express the genes for estrogen receptor, progesterone receptor or HER-2/ERBb2 (Her2/neu) receptor. About 85% of primary tumors are estrogen receptor positive; however about 71% of circulating tumor cells are estrogen receptor negative and 50% of circulating tumor cells are triple negative. The expression of Muc4, a high molecular weight glycoprotein on mammary epithelial cells, is upregulated with aberrant expression in over 95% of breast tumors: 40% in solid tumors and 70% in malignant effusions. These tumor-associated Muc4 expressing cells have aggressive clinical pathologic features associated with poor prognosis and elevated risk of recurrence. The risk of distant recurrence in women with triple-negative breast cancer is between two and three times that found in women with other breast cancers such as estrogen-receptor positive and HER-2/ERBb2 (Her2/neu) receptor positive (Dent R. et al. Clinical Cancer Research 13(15):4429-4434 (2007)). The most successful breast cancer treatments use drugs that directly target estrogen receptors. Because estrogen-negative breast cancer cells do not express these receptors, they are unresponsive to these treatments. Few, if any, effective clinical prospects exist for modulating the uncontrolled expression of Muc4 in over 95% of breast tumors and the aggressive clinical pathology of Muc4-containing cells.

The Muc4 glycoprotein is the human homologue of rat sialomucin complex (SMC). Sialomucin complex was originally isolated from highly malignant metastatic 13762 rat mammary adenocarcinoma ascites cells. It is a heterodimeric tumor cell surface glycoprotein composed of a high molecular weight peripheral sialomucin (ascites sialoglycoprotein-1, ASGP-1) tightly but noncovalently linked to a 120 kDa transmembrane N-glycosylated component ASGP-2. ASGP-1 is the major detectable glycoprotein that extends outwardly from the cell surface; whereas ASGP-2 is a slightly asymmetric globular protein having a Stokes radius of 4.6 nm. ASGP-2 contains two EGF-like domains and has been shown to act as a ligand for the tyrosine kinase p185neu. Sialomucin complex is present at very high levels in the ascites cells (>$10^6$ copies/cell), and the sialomucin has been implicated in the resistance to natural killer (NK) cells that play a major role in the rejection of tumors.

Muc4 consists of two subunits, the extracellular highly glycosylated mucin subunit (MUC4-α) with an extended rigid extracellular domain that can extend up to 2 micrometer over the cell membrane and a transmembrane subunit (Muc-4-β) containing three EGF-like domains. MUC4 is translated as a single precursor polypeptide, which is further cleaved at a GDPH site in two subunits before addition of O-linked oligosaccharides (Komatsu M. et al. Biochemical Journal 368:41-48 (2002)). Most normal tissues expressing Muc4/SMC produce both membrane bound and soluble forms of Muc4; however in malignant transformed rat tumors, Muc4/SMC is expressed predominantly in a membrane-bound form. It has been reported that ascites 13762 rat mammary adenocarcinoma cell surface sialomucin ASGP-1 is synthesized initially as a poorly glycosylated immature form, which is converted to a larger premature form with a $t_{1/2}$ of about 30 minutes and more slowly to the mature glycoprotein through O-glycosylation with a $t_{1/2}$ greater than 4 hours. Although 95% of ASGP-1 reaches the cell surface in 2 h, ASGP-1 reaches the cell surface in an incompletely glycosylated state, and additional oligosaccharides are added to the glycoprotein after ASGP-1 has reached the cell surface in a second process involving recycling and resialylation (Hull S. et al Journal of Biological Chemistry 25; 266(21):13580-13586 (1991)).

Muc4 is poorly expressed on the apical surface of mammary epithelial cells; however, it is overexpressed on a number of human breast tumors. Muc4 is expressed in a minority of solid breast tumors and is overexpressed in the majority of more aggressive tumor cells from malignant effusions. Overexpression of Muc4 has been shown to block cell-cell and cell-matrix interactions, protect tumor cells from immune surveillance and promote metastasis. Muc4 is also the putative ligand of the HER-2/ERBb2 (Her2/neu) oncogenic receptor found in about 25% of invasive breast cancers. Muc4 binds to and modulates phosphorylation of the HER-2/ERBb2 (Her2/neu) receptor and influences cell proliferation, tumor progression, and tumor cell morphology; however, overexpression of Muc4 does not interfere with surface expression of ErbB2 receptors. Overexpression of Muc4 sterically blocks anti-ErbB2 antibody binding to HER-2/ERBb2 (Her2/neu) oncogenic receptors such as seen with Herceptin (trastuzumab), possibly reducing its therapeutic effect. The expression of Muc4 protein is inversely correlated with trastuzumab binding capacity, it masks the binding epitopes of HER2 antibody, and it masks the epitope interaction of the HER-2/ERBb2 (Her2/neu) oncogenic receptor with other proteins such as EGRF (International Journal of Cancer 99:783-791 (2002)).

The glycan remodeling in breast cancer cells is complex when Muc4 is overexpressed. Compared with O-glycans from normal mucins whose O-glycans have an extended GlcNacβ1-6(Galβ1-3)GalNacα-Ser/Thr (core-2) structure, breast cancer-associated O-glycans are highly sialylated and sialylated Galβ1-3(Galβ1-3)GalNacα-Ser/Thr (core-1) prevails. An increase in the expression of α3-sialyltransferase ST3Gal-1, which acts on Galβ1-3(Galβ1-3)GalNacα-Ser/Thr (core 1), is characteristic of breast cancer cells that are most likely to metastasize (Brockhausen I EMBP Reports 7(6): 599-604 (2006)). Antibodies to the negatively charged sialylated epitopes or desialylation of mucin glycoproteins on the outer surface of the transformed cell have been shown to inhibit adhesion of metastatic cells to basement membranes.

The expression of Muc4 in stably transfected human ovarian cancer cells was analyzed by western blot, confocal microscopy and in vitro motility of transformed cells (Ponnusamy M P et al. British Journal of Cancer 99: 520-526 (2008). These Muc4-expressing cells demonstrated a significantly enhanced motility compared to control cells (P<0.05) and exhibited significant morphological changes associated with coordinated disassembly and reformation of the cortical actin organization. The increased motility is consistent with previous observations that silencing of Muc4 expression led to a three-fold decrease in cell motility (Singh, A P et al. Cancer Research 64, 622-630, Jan. 15, 2004). Muc4 plays an important role in tumor cell growth, behavior, and metastasis. Silencing Muc4 expression in cells that expresses high levels of MUC4 results in 1) a 3-fold decrease in the observed in vitro cell motility compared with control cells; 2) a significant decrease in tumor growth and metastatic properties when transplanted orthotopically into immunodeficient mice; and 3) reduced expression of its putative interacting partner, HER-2/ERBb2 (Her2/neu) (Bafna, S. et al. Cancer Research 68(22):9231-8 (2008)). Moreover, the in vivo tumorigenicity of Muc4-transfected cells injected in nude mice is significantly greater than with Muc4-deficient control cells. The mean tumor-free survival time over 40 days was significantly less (P<0.001) with injected Muc4-transfected cells (17.6 days) than with Muc4-deficient control cells (34.7 days). Only 7% of the mice injected with Muc4-transfected cells showed tumor-free survival at the end of 36 days, whereas 73% of the mice injected with Muc4-deficient control cells showed tumor-free survival at the end of 36 days. Tumor volume was consistently and significantly less with injected Muc4-deficient control cells than with injection of Muc4-transfected cells.

Published studies have demonstrated that the epithelial to mesenchymal transition of tumor-associated Muc4 is inhibited by TGF-β ALK5 inhibitors. These studies show that the TGF-β-induced epithelial to mesenchymal transition (EMT) in normal (NMuMG) cells was mediated though activation of the ALK5 receptor and Smad2 effector proteins. Inhibition of the phosphorylation of Smad2 by TGF-β ALK5 inhibitors was associated with less cell motility and cell morphological changes associated with EMT and inhibition of TGF-β signaling reduced Muc4 protein expression. These studies are consistent with other studies showing that silencing Muc4 expression results in a significant decrease in cell motility and metastatic properties in vivo. Studies have shown that the epithelial to mesenchymal transition in the normal mammary epithelial cells stimulated by TGF-β was abrogated by a general serine/threonine kinase and protein kinase inhibitor, staurosporine (Piek, E et al. Journal of Cell Science 112:4557-4568 (1999)), and that the TGF-β-induced epithelial to mesenchymal transition of NMuMG cells was mediated though activation of the ALK5 receptor and Smad2 effector proteins. TGF-β strongly induces Smad2 phosphorylation and its nuclear translocation. Using a series of specific small molecule inhibitors, it has been shown that only the general serine/threonine kinase and protein kinase inhibitor staurosporine exhibited a major effect on cell morphology and the expression of E-cadherin and β-catenin which render cells more motile and invasive. This finding was replicated in the regulation of the transformed sialomucin complex/rat Muc4 in mammary epithelial cells. Muc4 protein expression in transfected mammary epithelial cells (MEC) in a serum-free medium is low compared to Muc4 protein expression in 10% fetal calf serum, and Muc4 protein expression is inhibited by staurosporine (protein kinase C inhibitor-operating through TGF-β and Smad2) when activated in fetal calf serum (Zhu X. et al. Oncogene 19: 4354-4361 (2000)). Finally, it has been reported that only TGF-β1, TGF-β2, TGF-β3 among all type I TGF-β type receptors (TGF-β1, TGF-β2, TGF-β3, activin-A or BMP-7) induce EMT and growth inhibition in normal human cells (MCF-10A) and normal mouse epithelial cells (NMuMG) through the ALK5 mediated Smad pathway involving Smad2 (Valcourt U. et al. Molecular Biology of the Cell 16:1987-2002 (2002)). The selective ALK5 inhibitor SB431542 ((4-[4-(1,3-benzodioxol-5-yl)-5-(2-pyridinyl)-1H-imidazol-2-yl]benzamide), a potent and selective inhibitor of the transforming growth factor-β (TGF-β) type I receptor activin receptor-like kinase ALK5 having an $IC_{50}$=94 nM, inhibited the phosphorylation of Smad2 and morphological changes associated with EMT in NMuMG cells stimulated with TGF-β1.

A major disadvantage of nonselective small molecule inhibitors is their inherent cross-reactivity with other kinases. Given the exceptionally broad range of biological activities associated with TGF-β and its fundamental physiological roles, it is reasonable that nonselective TGF-β blockade could lead to loss of immune tolerance with uncontrolled activation of T and B cells. One benefit of using specific Smad2 regulated ALK5 inhibitors is the ability to select Smad-specific affecting the epithelial to mesenchymal transition responses in tumor cells without affecting other TGF-β signaling pathways; however, ALK5/Smad regulated TGF-β signaling is not limited to regulation in tumor cells (Goumans et al. Trends Cardiovascular Medicine 13(7):301-307 (2003); Lebrin F et al. Cardiovascular Research 65(3):599-608 (2005); Tsuchida K et al. Endocr. J. 55(1):11-21 (2008); Gauldie J et al. Biochem Soc Trans 35(Pt 4):661-4 (2007)). Because Muc4-expressing tumor cells do not express any specific protein receptors, selectively targeting these tumor cells and delivering specific inhibitors to regulate the Smad2 pathway is currently not possible.

It is an object of the present invention to provide compounds and methods for treating a subject having cancer comprising administering to the subject a tumor-targeted TGF-β ALK5 inhibitor-glycoconjugate in an amount effective in selectively targeting tumor-associated Muc4 glycoproteins, delivering TGF-β ALK5 inhibitors to the tumor and regulating the expression levels and glycosylation of tumor-associated Muc4.

It is a further object of the present invention to provide compounds and methods for modulating the epithelial-mesenchymal-transition of tumor cells and the progression of the cancer by reducing the migration, extravasation and metastatic dissemination of mesenchymal tumor cells.

It is a further object of the present invention to provide compounds and methods for treating a subject having a cancer in need of therapy thereof by administering to the subject a Muc4-targeted compound in an amount effective in reducing Muc4 expression or glycosylation.

BRIEF SUMMARY OF THE INVENTION

The present invention relates to compounds, pharmaceutical compositions and methods for treating a subject having cancer comprising administering to the subject a tumor-selective targeted TGF-β ALK5 inhibitor-glycoconjugate in an amount effective in selectively targeting tumor-associated Muc4 glycoproteins, delivering TGF-β ALK5 inhibitors to the tumor and regulating the expression levels and glycosylation of tumor-associated Muc4.

Tumor-selective targeted glycoconjugates useful in accordance with the present invention comprise compounds having the formula

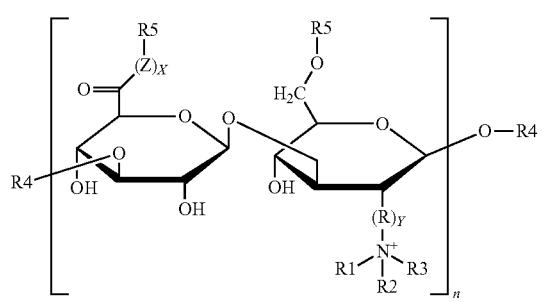

or compounds having the formula

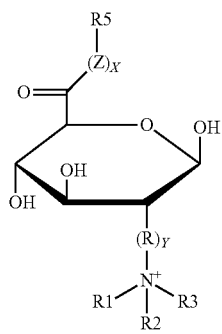

or compounds having the formula

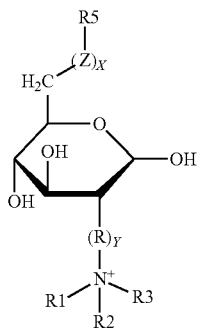

where R is an alkyl or alkylene, Y=0 or 1, $R_1$, $R_2$ and $R_3$ are independently hydrogen, alkyl, aryl, aralkyl and cycloalkyl, $R_4$ is independently hydrogen or lower alkyl, n is an integer from 1 to about 6, Z is a linker, X is 0 or 1, $R_5$ is hydrogen or a pharmacologically active residue of an ALK5 inhibitor, with the proviso said compound contains at least one pharmacologically active residue of an ALK5 inhibitor, and pharmaceutically acceptable salts thereof.

DETAILED DESCRIPTION OF THE INVENTION

A salient feature of the aberrantly expressed Muc4 oncoprotein is its altered glycosylation pattern which includes negatively-charged sialic acid molecules at the carbohydrate termini. This negatively charged surface of rigid glycans directly mitigates interaction of the cell surface with monoclonal antibodies and confounds the development of effective therapeutics for these cells. We have identified TGF-β ALK5 inhibitor-glycoconjugates that are capable of targeting the aberrantly expressed Muc4 oncoprotein and delivering the ALK5 inhibitor to regulate the transcription signaling through a specific TGF-β→ALK5→Smad2/Smad4 pathway. Our TGF-β ALK5 inhibitor-glycoconjugates, that carry a positive charge, can interact with the negatively charged surface of the Muc4-containing cell and deliver a therapeutically effective amount of inhibitor directly to the tumor cell. The selective targeting of these tumor cells advantageously avoids the possibility of undesired systemic interaction with ubiquitously expressed TGF-β.

The Muc4-targeted ALK5 inhibitor-glycoconjugates comprise an ALK5 inhibitor covalently attached to monosaccharides or oligosaccharides through a linkage (linker) that blocks the pharmacological activity of the inhibitor molecule in the circulation. Thus, the activity of the inhibitors at ubiquitously expressed TGF-β receptors is advantageously mitigated until they reach the tumor. Preferably, ALK5 inhibitors are attached to monosaccharides and oligosaccharides through an acid-labile linker. In this embodiment, the ALK5 inhibitor conjugates are expected to be stable in plasma under normal physiological conditions (pH 7.4); however, because they are acid-labile they are hydrolyzed in the acid environment of the tumor (pH ~5-6) where the ALK5 inhibitor is released. This is similar to the immunotargeting of tumors with doxorubicin conjugated to Lewis-Y-related tumor associated antigen monoclonal antibodies, polyethylene glycol or N-(2-hydroxypropyl)methacrylate through acid-labile linkers. These glycoconjugates are stable in plasma under physiological conditions; however, they are acid-labile and are hydrolyzed in the acid environment of the tumor where the doxorubicin is released. In these cases, the glycoconjugates are more cytotoxic than those with ester bonds that are hydrolyzed in plasma. It has long been known that the interstitial environment in malignant tumors is acidic as a result of accumulation of lactic acid and other acidic metabolites generated, and that solid tumors have regions of more acidic pH than are found in normal tissues. Tumor cells generally metabolize lipids and glucose differently from their normal counterparts. Tumor cells rapidly metabolize glucose, even in the presence of oxygen, which results in a low interstitial pH. The intracellular pH of cells in tumors is neutral-to-alkaline (pH 7.1-7.2), which is necessary for continued cell proliferation. In vivo measurements of extracellular pH have confirmed that the microenvironment in tumors is more acidic than in normal tissue with a pH of about 7.0 in tumors and 7.5 in normal tissue.

Normal epithelial cells are sensitive to TGF-β-mediated growth inhibition and are maintained in a homeostatic state. The tumor promoting effects of TGF-β include upregulation of vascular endothelial growth factor (VEGF) leading to angiogenesis, immunosuppression through effects on T-cell and natural killer cell activity, stimulation of platelet-derived (PDGF) and connective-tissue (CTGF) growth factors, production of metalloproteinases (MMPs) which contribute to extracellular matrix degradation and tumor cell invasion, and overexpression and aberrant glycosylation of Muc4. TGF-β also contributes to epithelial-mesenchymal-transition of the tumor cells and the progression of the disease by allowing migration, extravasation and metastatic dissemination of the mesenchymal tumor cells.

TGF-β-mediated Alk5-dependent signaling and SMAD2/SMAD3 phosphorylation has focused on inhibitors that are selective for the type I receptor kinase as a therapeutic target. Although many individual molecular scaffolds have been developed as small-molecule ALK5-receptor kinase inhibitors, each has easily recognized pharmacophores responsible for their pharmacological activity and specificity (Yingling J M et al. Nature Reviews/Drug Discovery Vol. 3:1011-1022 (2004)). Illustrative examples of our ALK5 inhibitors suitable for use in the present invention include imidazole-benzodioxol compounds, imidazole-quinoxaline compounds, pyrazole-pyrrolo compounds and thiazole type compounds.

In accordance with one aspect of the present invention, imidazole-benzodioxol type ALK5 inhibitors have the formula

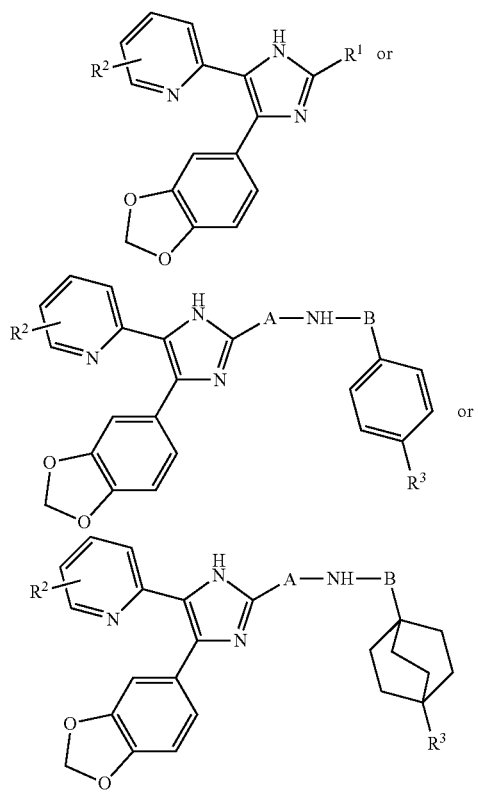

where $R^1$ is hydrogen or a lower alkyl having from 1 to about 5 carbon atoms, $R^2$ is hydrogen or lower alkyl having from 1 to about 5 carbon atoms and $R^3$ is an amide, nitrile, alkynyl having from 1 to about 3 carbon atoms, carboxyl or alkanol group having from 1 to about 5 carbon atoms, A is a direct bond or an alkyl having from 1 to about 5 carbon atoms and B is a direct bond or an alkyl having from 1 to about 5 carbon atoms. In separate preferred embodiments of the present invention, $R^2$ is hydrogen or methyl, A has 1 carbon atom and B is a direct bond to the benzyl group and $R^3$ is an amide. In a combined preferred embodiment of the present invention, $R^2$ is hydrogen or methyl, A has 1 carbon atom and B is a direct bond to the benzyl group.

In accordance with another aspect of the present invention, imidazole-quinoxaline type ALK5 inhibitors have the formula

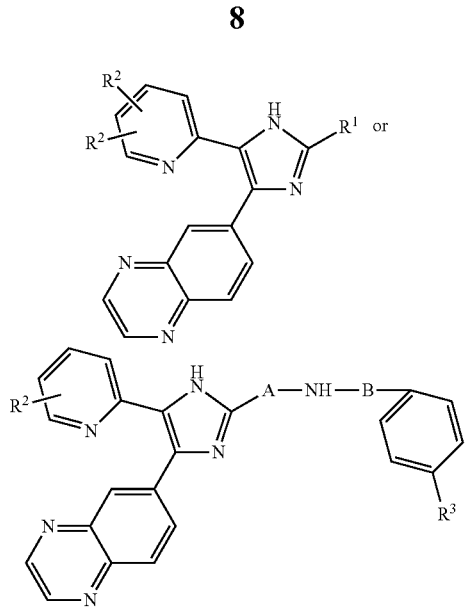

where $R^1$ is hydrogen or a lower alkyl having from 1 to about 5 carbon atoms, $R^2$ is hydrogen, halogen or lower alkyl having from 1 to about 5 carbon atoms and $R^3$ is an amide, nitrile, alkynyl having from 1 to about 3 carbon atoms, carboxyl or alkanol group having from 1 to about 5 carbon atoms, A is a direct bond or an alkyl having from 1 to about 5 carbon atoms and B is a direct bond or an alkyl having from 1 to about 5 carbon atoms. In separate preferred embodiments of the present invention, $R^2$ is hydrogen or methyl, halogens include fluorine or chlorine, A has 1 carbon atom and B is a direct bond to the benzyl group and $R^3$ is an amide. In a combined preferred embodiment of the present invention, $R^2$ is hydrogen or methyl, A has 1 carbon atom and B is a direct bond to the benzyl group.

In accordance with another aspect of the present invention, pyrazole type ALK5 inhibitors have the formula

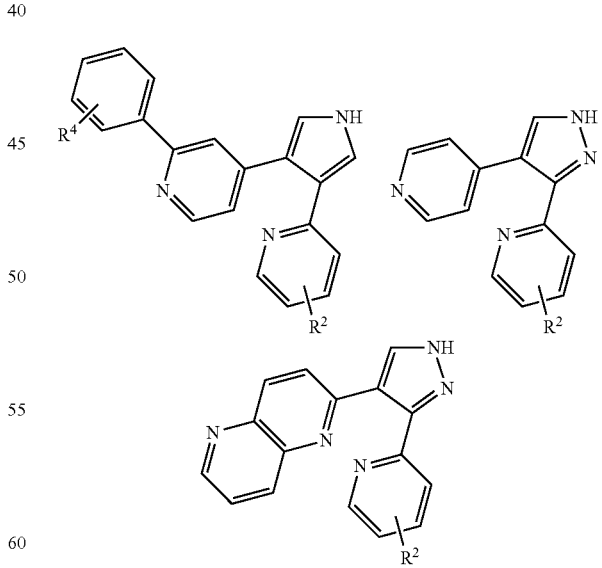

Where $R^2$ is hydrogen, halogen or lower alkyl having from 1 to about 5 carbon atoms, $R^4$ is hydrogen, halogen, lower alkyl having from 1 to about 5 carbon atoms, alkoxy having from 1 to about 5 carbon atoms, haloalkyl, carboxyl, carboxyalkylester, nitrile, alkylamine or a group having the formula

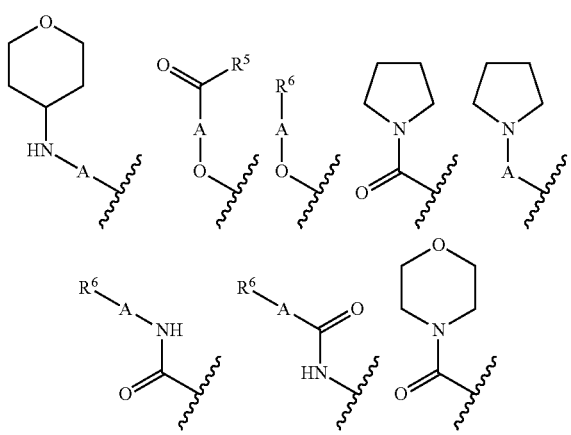

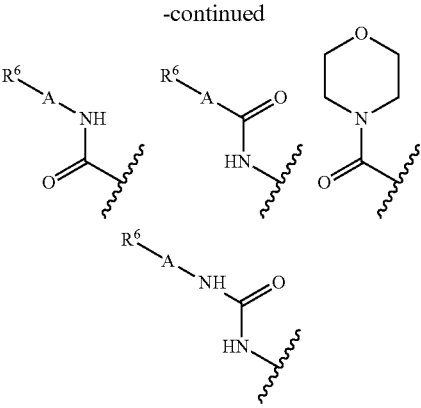

where $R^5$ is lower alkyl having from 1 to about 5 carbon atoms, halogen or morpholino, and $R^6$ is pyrole, cyclohexyl, morpholino, pyrazole, pyran, imidazole, oxane, pyrrolidinyl or alkylamine, and A is a direct bond or an alkyl having from 1 to about 5 carbon atoms.

In accordance with another aspect of the present invention, pyrazole-pyrrolo type ALK5 inhibitors have the formula

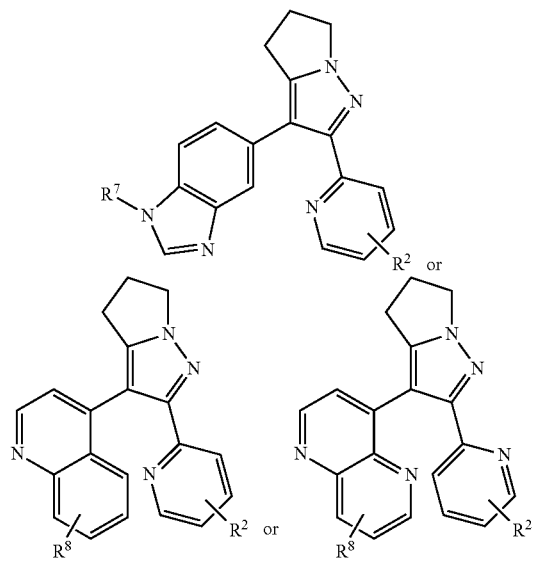

where $R^7$ is hydrogen, halogen, lower alkyl having from 1 to about 5 carbon atoms, alkanol, morpholino or alkylamine, $R^2$ is hydrogen, halogen or lower alkyl having from 1 to about 5 carbon atoms and $R^8$ is hydrogen, hydroxyl, amino, halogen or a group having the formula

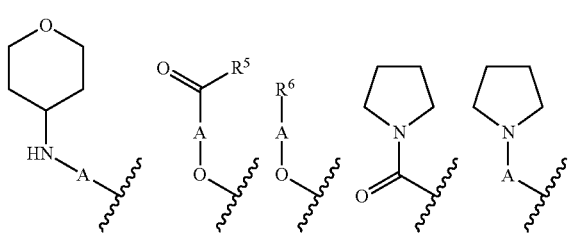

where R5 is piperazinyl, $R^6$ is morpholino, piperidinyl, piperazinyl, alkoxy, hydroxyl, oxane, halogen, thioalkyl or alkylamine, and A is a lower alkyl having from 1 to about 5 carbon atoms.

In accordance with another aspect of the present invention, Thiazole type ALK5 inhibitors have the formula

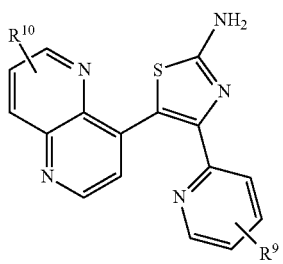

where $R^9$ is hydrogen, halogen or lower alkyl having from 1 to about 5 carbon atoms, and $R^{10}$ is hydrogen or lower alkyl having from 1 to about 5 carbon atoms.

The preparation and use of ALK5 inhibitors is well-known and well-documented in the scientific and patent literature. The following United States patents provide illustrations on the synthesis, properties and method of using ALK5 inhibitors, and are hereby incorporated by reference in their entirety, together with the patents cited therein: U.S. Pat. Nos. 7,365,066; 7,087,626; 7,368,445; 7,265,225; 7,405,299; 7,511,056; 7,612,094 and 7,691,865. Several ALK5 inhibitors are commercially available, including SB-525334 (CAS 356559-20-1), SB-505124 (CAS 694433-59-5), SB-431542 (CAS 301836-41-9), SB-202474 (EMD4 Biosciences Merck KGaA, Darmstadt, Germany), LY-364947 (CAS 396129-53-6), IN-1130, GW-788388 and D4476 (EMD4 Biosciences Merck KGaA, Darmstadt, Germany).

Alk5 inhibitors useful in accordance with the present invention include:
4-(4-(2,3-dihydrobenzo[b][1,4]dioxin-6-yl)-5-(pyridin-2-yl)-1H-imidazol-2-yl)benzamide
4-((4-(benzo[d][1,3]dioxol-5-yl)-5-(6-methylpyridin-2-yl)-1H-imidazol-2-ylamino)methyl)benzonitrile
3-((4-(benzo[d][1,3]dioxol-5-yl)-5-(6-methylpyridin-2-yl)-1H-imidazol-2-yl)methylamino)benzonitrile
3-((4-(benzo[d][1,3]dioxol-5-yl)-5-(6-methylpyridin-2-yl)-1H-imidazol-2-yl)methylamino)benzamide
4-((4-(benzo[d][1,3]dioxol-5-yl)-5-(6-ethylpyridin-2-yl)-1H-imidazol-2-yl)methylamino)benzamide
4-(4-(benzo[d][1,3]dioxol-5-yl)-5-(pyridin-2-yl)-1H-imidazol-2-yl)benzamide 3-((4-(benzo[d][1,3]dioxol-5-yl)-5-(6-methylpyridin-2-yl)-1H-imidazol-2-ylamino)methyl)benzonitrile
4-(4-(benzo[d][1,3]dioxol-5-yl)-5-(pyridin-2-yl)-1H-imidazol-2-yl)benzamide
4-((4-(benzo[d][1,3]dioxol-5-yl)-5-(6-methylpyridin-2-yl)-1H-imidazol-2-ylamino)methyl)benzonitrile
4-(4-(3a,4-dihydrobenzo[d][1,3]dioxol-5-yl)-5-(6-ethylpyridin-2-yl)-1H-imidazol-2-yl)methylamino)benzamide
N-((4-(3a,4-dihydrobenzo[d][1,3]dioxol-5-yl)-5-(6-methylpyridin-2-yl)-1H-imidazol-2-yl)methyl)-4-ethynylaniline
3-((4-(3a,4-dihydrobenzo[d][1,3]dioxol-5-yl)-5-(6-ethylpyridin-2-yl)-1H-imidazol-2-yl)methylamino)benzonitrile
4-(3a,4-dihydrobenzo[d][1,3]dioxol-5-yl)-N-(4-ethynylbenzyl)-5-(6-methylpyridin-2-yl)-1H-imidazol-2-amine
4-((4-(3a,4-dihydrobenzo[d][1,3]dioxol-5-yl)-5-(6-methylpyridin-2-yl)-1H-imidazol-2-ylamino)methyl)benzonitrile
4-((4-(3a,4-dihydrobenzo[d][1,3]dioxol-5-yl)-5-(6-methylpyridin-2-yl)-1H-imidazol-2-ylamino)methyl)benzonitrile
4-((4-(3a,4-dihydrobenzo[d][1,3]dioxol-5-yl)-5-(6-methylpyridin-2-yl)-1H-imidazol-2-yl)methylamino)benzamide
4-((4-(3a,4-dihydrobenzo[d][1,3]dioxol-5-yl)-5-(6-ethylpyridin-2-yl)-1H-imidazol-2-yl)methylamino)benzonitrile
4-(4-(3a,4-dihydrobenzo[d][1,3]dioxol-5-yl)-5-(pyridin-2-yl)-1H-imidazol-2-yl)benzoic acid
4-(4-(benzo[d][1,3]dioxol-5-yl)-5-(pyridin-2-yl)-1H-imidazol-2-yl)benzamide
4-(4-(benzo[d][1,3]dioxol-5-yl)-5-(6-methylpyridin-2-yl)-1H-imidazol-2-yl)methylamino)benzamide
4-(4-(benzo[d][1,3]dioxol-5-yl)-5-(pyridin-2-yl)-1H-imidazol-2-yl)benzoic acid
4-(4-(benzo[d][1,3]dioxol-5-yl)-5-(pyridin-2-yl)-1H-imidazol-2-yl)benzoic acid
4-(4-(benzo[d][1,3]dioxol-5-yl)-5-(pyridin-2-yl)-1H-imidazol-2-yl)benzamide
3-((4-(benzo[d][1,3]dioxol-5-yl)-5-(6-ethylpyridin-2-yl)-1H-imidazol-2-yl)methylamino)benzamide
3-((4-(benzo[d][1,3]dioxol-5-yl)-5-(6-methylpyridin-2-yl)-1H-imidazol-2-ylamino)methyl)benzonitrile
(4-(4-(benzo[d][1,3]dioxol-5-yl)-5-(pyridin-2-yl)-1H-imidazol-2-yl)phenyl)methanol
4-((4-(benzo[d][1,3]dioxol-5-yl)-5-(6-methylpyridin-2-yl)-1H-imidazol-2-yl)methylamino)benzamide
4-(4-(benzo[d][1,3]dioxol-5-yl)-5-(pyridin-2-yl)-1H-imidazol-2-yl)benzonitrile
2-(4-(benzo[d][1,3]dioxol-5-yl)-2-tert-butyl-1H-imidazol-5-yl)-6-methylpyridine
3-((4-(benzo[d][1,3]dioxol-5-yl)-5-(6-ethylpyridin-2-yl)-1H-imidazol-2-yl)methylamino)benzamide
4-((4-(benzo[d][1,3]dioxol-5-yl)-5-(6-ethylpyridin-2-yl)-1H-imidazol-2-yl)methylamino)benzonitrile
3-((4-(benzo[d][1,3]dioxol-5-yl)-5-(6-ethylpyridin-2-yl)-1H-imidazol-2-yl)methylamino)benzonitrile
4-((4-(benzo[d][1,3]dioxol-5-yl)-5-(6-methylpyridin-2-yl)-1H-imidazol-2-yl)methylamino)benzonitrile
2-(4-(benzo[d][1,3]dioxol-5-yl)-2-tert-butyl-1H-imidazol-5-yl)-6-methylpyridine
3-((5-(6-methylpyridin-2-yl)-4-(quinoxalin-6-yl)-1H-imidazol-2-yl)methyl)benzamide
4-((5-(6-ethylpyridin-2-yl)-4-(quinoxalin-6-yl)-1H-imidazol-2-yl)methylamino)benzamide
4-((5-(6-methylpyridin-2-yl)-4-(1,4,4a,8a-tetrahydroquinoxalin-6-yl)-1H-imidazol-2-yl)methylamino)benzamide
4-((5-(6-ethylpyridin-2-yl)-4-(quinoxalin-6-yl)-1H-imidazol-2-yl)methylamino)benzamide
3-((5-(6-ethylpyridin-2-yl)-4-(quinoxalin-6-yl)-1H-imidazol-2-yl)methylamino)benzamide
4-((5-(6-methylpyridin-2-yl)-4-(quinoxalin-6-yl)-1H-imidazol-2-yl)methylamino)benzonitrile
3-((5-(6-ethylpyridin-2-yl)-4-(quinoxalin-6-yl)-1H-imidazol-2-yl)methylamino)benzonitrile
4-((5-(6-methylpyridin-2-yl)-4-(quinoxalin-6-yl)-1H-imidazol-2-yl)methylamino)benzamide
3-((5-(6-methylpyridin-2-yl)-4-(quinoxalin-6-yl)-1H-imidazol-2-yl)methylamino)benzamide
3-((5-(6-methylpyridin-2-yl)-4-(quinoxalin-6-yl)-1H-imidazol-2-yl)methyl)benzamide
3-((5-(6-methylpyridin-2-yl)-4-(quinoxalin-6-yl)-1H-imidazol-2-yl)methylamino)benzonitrile
3-((5-(6-methylpyridin-2-yl)-4-(quinoxalin-6-yl)-1H-imidazol-2-yl)methylamino)benzamide
6-(2-tert-butyl-5-(6-methylpyridin-2-yl)-1H-imidazol-4-yl)quinoxaline
4-(5-fluoro-6-methylpyridin-2-yl)-5-(quinoxalin-6-yl)-1H-imidazol-2-amine
4-((5-(6-ethylpyridin-2-yl)-4-(quinoxalin-6-yl)-1H-imidazol-2-yl)methylamino)benzonitrile
4-((5-(6-methylpyridin-2-yl)-4-(quinoxalin-6-yl)-1H-imidazol-2-yl)methylamino)benzonitrile
3-((5-(6-methylpyridin-2-yl)-4-(quinoxalin-6-yl)-1H-imidazol-2-yl)methylamino)benzamide
4-((5-(6-ethylpyridin-2-yl)-4-(1,4,4a,8a-tetrahydroquinoxalin-6-yl)-1H-imidazol-2-yl)methylamino)benzonitrile
N-((5-(6-ethylpyridin-2-yl)-4-(1,4,4a,8a-tetrahydroquinoxalin-6-yl)-1H-imidazol-2-yl)methyl)-3-ethynylaniline
4-((5-(6-ethylpyridin-2-yl)-4-(1,4,4a,8a-tetrahydroquinoxalin-6-yl)-1H-imidazol-2-yl)methylamino)benzamide
2-(3-(pyridin-2-yl)-1H-pyrazol-4-yl)-1,5-naphthyridine
3-((5-(6-Methylpyridin-2-yl)-4-(1,5-naphthyridin-2-yl)-1H-pyrazol-1-yl)methyl)benzamide
2-(3-(6-methylpyridin-2-yl)-1H-pyrazol-4-yl)-1,5-naphthyridine
3-((3-(6-Methylpyridin-2-yl)-4-(1,5-naphthyridin-2-yl)-1H-pyrazol-1-yl)methyl)benzamide
2-(3-(6-methylpyridin-2-yl)-1H-pyrazol-4-yl)-1,5-naphthyridine
2-(3-(pyridin-2-yl)-1H-pyrazol-4-yl)-1,5-naphthyridine
3-((5-(6-Methylpyridin-2-yl)-4-(1,5-naphthyridin-2-yl)-1H-pyrazol-1-yl)methyl)benzonitrile
2-(3-(6-methylpyridin-2-yl)-1H-pyrazol-4-yl)-1,5-naphthyridine
2-(3-(pyridin-2-yl)-1H-pyrazol-4-yl)-1,5-naphthyridine
3-((3-(6-Methylpyridin-2-yl)-4-(1,5-naphthyridin-2-yl)-1H-pyrazol-1-yl)methyl)benzonitrile
2-(3-(pyridin-2-yl)-1H-pyrazol-4-yl)-1,5-naphthyridine
dimethyl-{2-[(4-{4-[3-(pyridin-2-yl)-1H-pyrazol-4-yl]-2-pyridinyl}phenoxy)ethyl}amine
2-(4-chlorophenyl)-4-(3-(pyridin-2-yl)-1H-pyrazol-4-yl)pyridine
[(4-{4-[3-(pyridin-2-yl)-1H-pyrazol-4-yl]pyridin-2-yl}phenyl)-methyl]tetrahydro-2H-pyran-4-ylamine
2-{4-[(2-chloroethyl)oxy]phenyl}-4-[3-(pyridin-2-yl)-1H-pyrazol-4-yl]pyridine
N-(2-methoxyethyl)-4-(4-(3-(pyridin-2-yl)-1H-pyrazol-4-yl)pyridin-2-yl)benzamide
2-morpholin-1-yl-N-{4-[4-(3-pyridin-2-yl-1H-pyrazol-4-yl)-pyridin-2-yl]phenyl}acetamide
2-[4-methylphenyl]-4-(3-pyridin-2-yl-1H-pyrazol-4-yl pyridine 4-(3-(pyridin-2-yl)-1H-pyrazol-4-yl)-2-(3-(trifluoromethyl)phenyl)pyridine
N-(2-methoxyethyl)-4-(4-(3-(pyridin-2-yl)-1H-pyrazol-4-yl)pyridin-2-yl)benzamide
2-(4-chlorophenyl)-4-(3-(pyridin-2-yl)-1H-pyrazol-4-yl)pyridine
2-[2-(trifluoromethyl)phenyl]-4-(3-pyridin-2-yl-1H-pyrazol-4-yl)pyridine
2-(2-fluorophenyl)-4-(3-(pyridin-2-yl)-1H-pyrazol-4-yl)pyridine
2-(4-(2-(1H-imidazol-1-yl)ethoxy)phenyl)-4-(3-(pyridin-2-yl)-1H-pyrazol-4-yl)pyridine
2-[4-isopropylphenyl]-4-[3-(pyridin-2-yl)-1H-pyrazol-4-yl]pyridine
N-(4-(4-(3-(pyridin-2-yl)-1H-pyrazol-4-yl)pyridin-2-yl)phenyl)tetrahydro-2H-pyran-4-carboxamide
2-phenyl-4-(3-(pyridin-2-yl)-1H-pyrazol-4-yl)pyridine
2-(4-(2-cyclohexylethoxy)phenyl)-4-(3-(pyridin-2-yl)-1H-pyrazol-4-yl)pyridine
2-pyrrolidin-1-yl-N-{4-[4-(3-pyridin-2-yl-1H-pyrazol-4-yl)-pyridin-2-yl]phenyl}acetamide
4-[3-(pyridin-2-yl)-1H-pyrazol-4-yl]-2-[4-(1-pyrrolidinylmethyl)phenyl]pyridine
2-(3-methoxyphenyl)-4-(3-(pyridin-2-yl)-1H-pyrazol-4-yl)pyridine
4-(4-(3-(pyridin-2-yl)-1H-pyrazol-4-yl)pyridin-2-yl)benzonitrile
4-(3-(pyridin-2-yl)-1H-pyrazol-4-yl)-2-(4-(trifluoromethyl)phenyl)pyridine
2-(2-fluorophenyl)-4-(3-(pyridin-2-yl)-1H-pyrazol-4-yl)pyridine
N-methyl-4-(4-(3-(pyridin-2-yl)-1H-pyrazol-4-yl)pyridin-2-yl)-N-(tetrahydro-2H-pyran-4-yl)benzamide
2-(4-fluorophenyl)-4-(3-(pyridin-2-yl)-1H-pyrazol-4-yl)pyridine
4-(3-(pyridin-2-yl)-1H-pyrazol-4-yl)-2-(3-(trifluoromethyl)phenyl)pyridine
2-(3-methoxyphenyl)-4-(3-(pyridin-2-yl)-1H-pyrazol-4-yl)pyridine
N-methyl-4-(4-(3-(pyridin-2-yl)-1H-pyrazol-4-yl)pyridin-2-yl)-N-(tetrahydro-2H-pyran-4-yl)benzamide
2-[3-methylphenyl]-4-(3-pyridin-2-yl-1H-pyrazol-4-yl)pyridine
4-{2-[(4-{4-[3-(pyridin-2-yl)-1H-pyrazol-4-yl]-pyridin-2-yl}-phenyl)oxy]ethyl}morpholine
2-(2-methylphenyl)-4-[3-(pyridin-2-yl)-1H-pyrazol-4-yl]pyridine
4-(3-(pyridin-2-yl)-1H-pyrazol-4-yl)-2-(4-(trifluoromethyl)phenyl)pyridine
4-(4-(3-(pyridin-2-yl)-1H-pyrazol-4-yl)pyridin-2-yl)benzonitrile
1-(4-(4-(3-(pyridin-2-yl)-1H-pyrazol-4-yl)pyridin-2-yl)phenoxy)propan-2-one
4-(4-(4-(3-(pyridin-2-yl)-1H-pyrazol-4-yl)pyridin-2-yl)benzyl)morpholine
4-(4-(3-(pyridin-2-yl)-1H-pyrazol-4-yl)pyridin-2-yl)-N-(tetrahydro-2H-pyran-4-yl)benzamide
N-(4-(4-(3-(pyridin-2-yl)-1H-pyrazol-4-yl)pyridin-2-yl)benzyl)tetrahydro-2H-pyran-3-amine
1-(4-(4-(3-(pyridin-2-yl)-1H-pyrazol-4-yl)pyridin-2-yl)phenoxy)propan-2-one
4-(3-(pyridin-2-yl)-1H-pyrazol-4-yl)-2-(4-(2-(pyrrolidin-1-yl)ethoxy)phenyl)pyridine
4-(3-(pyridin-2-yl)-1H-pyrazol-4-yl)-2-(4-(2-(pyrrolidin-1-yl)ethoxy)phenyl)pyridine
4-(4-(3-(pyridin-2-yl)-1H-pyrazol-4-yl)pyridin-2-yl)benzyl)morpholine
4-[4-(3-pyridin-2-yl-1H-pyrazol-4-yl)pyridin-2-yl]benzoic acid methyl ester
4-(4-(3-(pyridin-2-yl)-1H-pyrazol-4-yl)pyridin-2-yl)benzoic acid
N-(4-(4-(3-(pyridin-2-yl)-1H-pyrazol-4-yl)pyridin-2-yl)phenyl)-2-(pyrrolidin-1-yl)acetamide
N,N-dimethyl-3-(3-(4-(3-(pyridin-2-yl)-1H-pyrazol-4-yl)pyridin-2-yl)phenyl)propan-1-amine
2-[4-methoxyphenyl]-4-(3-pyridin-2-yl-1H-pyrazol-4-yl)pyridine
4-(3-(pyridin-2-yl)-1H-pyrazol-4-yl)quinoline
4-(1-benzyl-3-(pyridin-2-yl)-1H-pyrazol-4-yl)quinoline
3-((5-(6-Methylpyridin-2-yl)-4-(quinolin-6-yl)-1H-pyrazol-1-yl)methyl)benzamide
4-(3-(pyridin-2-yl)-1H-pyrazol-4-yl)quinoline
3-((4-(6-Methylpyridin-2-yl)-3-(quinolin-6-yl)-1H-pyrazol-1-yl)methyl)benzamide
3-((5-(6-Methylpyridin-2-yl)-4-(quinolin-6-yl)-1H-pyrazol-1-yl)methyl)benzonitrile
4-(3-(pyridin-2-yl)-1H-pyrazol-4-yl)quinoline
3-((3-(6-Methylpyridin-2-yl)-4-(quinolin-6-yl)-1H-pyrazol-1-yl)methyl)benzamide
4-(3-(5-fluoropyridin-2-yl)-1H-pyrazol-4-yl)quinoline
4-(5-cyclopropyl-3-(pyridin-2-yl)-1H-pyrazol-4-yl)quinoline
4-(4-(pyridin-2-yl)-1H-pyrazol-3-yl)quinoline
4-(3-(5-fluoropyridin-2-yl)-1H-pyrazol-4-yl)quinoline
4-(1-benzyl-3-(pyridin-2-yl)-1H-pyrazol-4-yl)quinoline
4-(3-(5-fluoropyridin-2-yl)-1H-pyrazol-4-yl)quinoline
4-(3-(pyridin-2-yl)-1H-pyrazol-4-yl)quinoline
4-[3-(6-Bromo-pyridin-2-yl)-1H-pyrazol-4-yl]-quinoline
4-(3-(5-chloropyridin-2-yl)-1H-pyrazol-4-yl)quinoline
4-(1-benzyl-3-(pyridin-2-yl)-1H-pyrazol-4-yl)quinoline
4-(3-(5-fluoropyridin-2-yl)-1H-pyrazol-4-yl)quinoline
4-(3-(3-(trifluoromethyl)phenyl)-1H-pyrazol-4-yl)quinoline
3-((4-(6-Methylpyridin-2-yl)-3-(quinolin-6-yl)-1H-pyrazol-1-yl)methyl)benzonitrile
4-[3-(6-Methyl-pyridin-2-yl)-1H-pyrazol-4-yl]-quinoline
4-(3-(pyridin-2-yl)-1H-pyrazol-4-yl)quinoline
4-(1-benzyl-3-(pyridin-2-yl)-1H-pyrazol-4-yl)quinoline
4-(3-(3-(trifluoromethyl)phenyl)-1H-pyrazol-4-yl)quinoline
3-((3-(6-Methylpyridin-2-yl)-4-(quinolin-6-yl)-1H-pyrazol-1-yl)methyl)benzonitrile
4-(3-(thiophen-2-yl)-1H-pyrazol-4-yl)quinoline
4-[5-Methyl-3-(6-methyl-pyridin-2-yl)-1H-pyrazol-4-yl]-quinoline
4-[5-Methyl-3-(6-methyl-pyridin-2-yl)-1H-pyrazol-4-yl]-quinoline
4-(3-phenyl-1H-pyrazol-4-yl)quinoline
4-(3-(thiophen-2-yl)-1H-pyrazol-4-yl)quinoline
4-(3-phenyl-1H-pyrazol-4-yl)quinoline
4-[5-Methyl-3-(6-methyl-pyridin-2-yl)-1H-pyrazol-4-yl]-quinoline
1,2-dimethyl-4-phenyl-5-(quinoxalin-6-yl)-1H-pyrazol-3(2H)-one
4-(3-chlorophenyl)-1,2-dimethyl-5-(quinoxalin-6-yl)-1H-pyrazol-3(2H)-one
4-(3-fluorophenyl)-1,2-dimethyl-5-(quinoxalin-6-yl)-1H-pyrazol-3(2H)-one
methyl 3-(1,2-dimethyl-3-oxo-5-(quinoxalin-6-yl)-2,3-dihydro-1H-pyrazol-4-yl)benzoate
1,2-dimethyl-4-(2-methylpyridin-4-yl)-5-(quinoxalin-6-yl)-1H-pyrazol-3(2H)-one
1,2-dimethyl-5-(quinoxalin-6-yl)-4-m-tolyl-1H-pyrazol-3(2H)-one
4-(2-hydroxyphenyl)-1,2-dimethyl-5-(quinoxalin-6-yl)-1H-pyrazol-3(2H)-one 4-(1H-indol-5-yl)-1,2-dimethyl-5-(quinoxalin-6-yl)-1H-pyrazol-3(2H)-one
1-(3-(1,2-dimethyl-3-oxo-5-(quinoxalin-6-yl)-2,3-dihydro-1H-pyrazol-4-yl)phenyl)-3-methylurea
4-(3-acetylphenyl)-1,2-dimethyl-5-(quinoxalin-6-yl)-1H-pyrazol-3(2H)-one
4-(3-(methoxymethyl)phenyl)-1,2-dimethyl-5-(quinoxalin-6-yl)-1H-pyrazol-3(2H)-one
4-(2-aminophenyl)-1,2-dimethyl-5-(quinoxalin-6-yl)-1H-pyrazol-3(2H)-one
3-(1,2-dimethyl-3-oxo-5-(quinoxalin-6-yl)-2,3-dihydro-1H-pyrazol-4-yl)benzonitrile
4-(3-methoxyphenyl)-1,2-dimethyl-5-(quinoxalin-6-yl)-1H-pyrazol-3(2H)-one
1,2-dimethyl-4-(pyridin-3-yl)-5-(quinoxalin-6-yl)-1H-pyrazol-3(2H)-one
1,2-dimethyl-5-(quinoxalin-6-yl)-4-(thiophen-2-yl)-1H-pyrazol-3(2H)-one
1,2-dimethyl-5-(quinoxalin-6-yl)-4-(3-vinylphenyl)-1H-pyrazol-3(2H)-one
2-(3-(1,2-dimethyl-3-oxo-5-(quinoxalin-6-yl)-2,3-dihydro-1H-pyrazol-4-yl)phenyl)acetonitrile
N-(3-(1,2-dimethyl-3-oxo-5-(quinoxalin-6-yl)-2,3-dihydro-1H-pyrazol-4-yl)phenyl)acetamide
3-(1,2-dimethyl-3-oxo-5-(quinoxalin-6-yl)-2,3-dihydro-1H-pyrazol-4-yl)benzamide
1,2-dimethyl-5-(quinoxalin-6-yl)-4-(thiophen-3-yl)-1H-pyrazol-3(2H)-one
4-(furan-2-yl)-1,2-dimethyl-5-(quinoxalin-6-yl)-1H-pyrazol-3(2H)-one
4-(furan-3-yl)-1,2-dimethyl-5-(quinoxalin-6-yl)-1H-pyrazol-3(2H)-one
4-(benzo[c][1,2,5]oxadiazol-5-yl)-1,2-dimethyl-5-(quinoxalin-6-yl)-1H-pyrazol-3(2H)-one
N-(3-(1,2-dimethyl-3-oxo-5-(quinoxalin-6-yl)-2,3-dihydro-1H-pyrazol-4-yl)phenyl)ethanesulfonamide
1,2-dimethyl-5-(quinoxalin-6-yl)-4-(3-(trifluoromethyl)phenyl)-1H-pyrazol-3(2H)-one
4-(4-aminophenyl)-1,2-dimethyl-5-(quinoxalin-6-yl)-1H-pyrazol-3(2H)-one
4-(3-ethylphenyl)-1,2-dimethyl-5-(quinoxalin-6-yl)-1H-pyrazol-3(2H)-one
4-(3-hydroxyphenyl)-1,2-dimethyl-5-(quinoxalin-6-yl)-1H-pyrazol-3(2H)-one
4-(3-aminophenyl)-1,2-dimethyl-5-(quinoxalin-6-yl)-1H-pyrazol-3(2H)-one
4-(3-isopropylphenyl)-1,2-dimethyl-5-(quinoxalin-6-yl)-1H-pyrazol-3(2H)-one
2-(1,2-dimethyl-3-oxo-5-(quinoxalin-6-yl)-2,3-dihydro-1H-pyrazol-4-yl)benzonitrile
1,2-dimethyl-4-(6-methylpyridin-2-yl)-5-(quinoxalin-6-yl)-1H-pyrazol-3(2H)-one
N-(3-(1,2-dimethyl-3-oxo-5-(quinoxalin-6-yl)-2,3-dihydro-1H-pyrazol-4-yl)phenyl)methanesulfonamide
1,2-dimethyl-4-(pyridin-2-yl)-5-(quinoxalin-6-yl)-1H-pyrazol-3(2H)-one
1,2-dimethyl-4-(3-(methylthio)phenyl)-5-(quinoxalin-6-yl)-1H-pyrazol-3(2H)-one
4-(3-(aminomethyl)phenyl)-1,2-dimethyl-5-(quinoxalin-6-yl)-1H-pyrazol-3(2H)-one
4-(4-hydroxyphenyl)-1,2-dimethyl-5-(quinoxalin-6-yl)-1H-pyrazol-3(2H)-one
4-(benzo[b]thiophen-3-yl)-1,2-dimethyl-5-(quinoxalin-6-yl)-1H-pyrazol-3(2H)-one
4-(3-bromophenyl)-1,2-dimethyl-5-(quinoxalin-6-yl)-1H-pyrazol-3(2H)-one
4-(3-(hydroxymethyl)phenyl)-1,2-dimethyl-5-(quinoxalin-6-yl)-1H-pyrazol-3(2H)-one
1-methyl-5-(2-pyridin-2-yl-5,6-dihydro-4H-pyrrolo[1,2-b]pyrazol-3-yl)-1H-benzoimidazole
1-methyl-6-[2-(6-methylpyridin-2-yl)-5,6-dihydro-4H-pyrrolo-[1,2-b]pyrazol-3-yl]-1H-benzoimidazole
N,N-diethyl-3-(6-(2-(6-methylpyridin-2-yl)-5,6-dihydro-4H-pyrrolo[1,2-b]pyrazol-3-yl)-1H-benzo[d]imidazol-1-yl)propan-1-amine
N,N-diethyl-3-(6-(2-(6-methylpyridin-2-yl)-5,6-dihydro-4H-pyrrolo[1,2-b]pyrazol-3-yl)-1H-benzo[d]imidazol-1-yl)propan-1-amine
N,N-diethyl-3-(6-(2-(6-methylpyridin-2-yl)-5,6-dihydro-4H-pyrrolo[1,2-b]pyrazol-3-yl)-1H-benzo[d]imidazol-1-yl)propan-1-amine
3-[6-(2-pyridin-2-yl-5,6-dihydro-4H-pyrrolo[1,2-b]pyrazol-3-yl)-benzoimidazol-1-yl]-propan-1-ol
3-[6-(2-pyridin-2-yl-5,6-dihydro-4H-pyrrolo[1,2-b]pyrazol-3-yl)-benzoimidazol-1-yl]-propan-1-ol
3-(6-(2-(6-methylpyridin-2-yl)-5,6-dihydro-4H-pyrrolo[1,2-b]pyrazol-3-yl)-1H-benzo[d]imidazol-1-yl)propan-1-ol
1-methyl-5-(2-pyridin-2-yl-5,6-dihydro-4H-pyrrolo[1,2-b]pyrazol-3-yl)-1H-benzoimidazole
3-(6-(2-(6-methylpyridin-2-yl)-5,6-dihydro-4H-pyrrolo[1,2-b]pyrazol-3-yl)-1H-benzo[d]imidazol-1-yl)propan-1-ol
1-methyl-5-(2-pyridin-2-yl-5,6-dihydro-4H-pyrrolo[1,2-b]pyrazol-3-yl)-1H-benzoimidazole dimethyl-{3-[6-(2-pyridin-2-yl-5,6-dihydro-4H-pyrrolo[1,2-b]pyrazol-3-yl)-benzoimidazol-1-yl]-propyl}-amine
5-[2-(6-methylpyridin-2-yl)-5,6-dihydro-4H-pyrrolo[1,2-b]pyrazol-3-yl]-1-[3-(tetrahydro-pyran-2-yloxy)-propyl]-1H-benzoimidazole
3-[6-(2-pyridin-2-yl-5,6-dihydro-4H-pyrrolo[1,2-b]pyrazol-3-yl)-benzoimidazol-1-yl]-propan-1-ol
5-(2-pyridin-2-yl-5,6-dihydro-4H-pyrrolo[1,2-b]pyrazol-3-yl)-1-[3-(tetrahydro-pyran-2-yloxy)-propyl]-1H-benzoimidazole
6-[2-(6-methyl-pyridin-2-yl)-5,6-dihydro-4H-pyrrolo[1,2-b]pyrazol-3-yl]-1-(3-pyrrolidin-1-yl-propyl)-1H-benzoimidazole
1-methyl-6-[2-(6-methylpyridin-2-yl)-5,6-dihydro-4H-pyrrolo-[1,2-b]pyrazol-3-yl]-1H-benzoimidazole
1-methyl-6-(2-pyridin-2-yl-5,6-dihydro-4H-pyrrolo[1,2-b]pyrazol-3-yl)-1Hbenzoimidazole
N,N-diethyl-3-(6-(2-(6-methylpyridin-2-yl)-5,6-dihydro-4H-pyrrolo[1,2-b]pyrazol-3-yl)-1H-benzo[d]imidazol-1-yl)propan-1-amine
5-(2-pyridin-2-yl-5,6-dihydro-4H-pyrrolo[1,2-b]pyrazol-3-yl)-1-[3-(tetrahydro-pyran-2-yloxy)-propyl]-1H-benzoimidazole
6-[2-(6-methyl-pyridin-2-yl)-5,6-dihydro-4H-pyrrolo[1,2-b]pyrazol-3-yl]-1-(3-pyrrolidin-1-yl-propyl)-1H-benzoimidazole
5-(2-pyridin-2-yl-5,6-dihydro-4H-pyrrolo[1,2-b]pyrazol-3-yl)-1-[3-(tetrahydro-pyran-2-yloxy)-propyl]-1H-benzoimidazole
6-(2-(pyridin-2-yl)-5,6-dihydro-4H-pyrrolo[1,2-b]pyrazol-3-yl)-1-(3-(pyrrolidin-1-yl)propyl)-1H-benzo[d]imidazole
5-(2-(pyridin-2-yl)-5,6-dihydro-4H-pyrrolo[1,2-b]pyrazol-3-yl)-1H-benzo[d]imidazole
3-(6-(2-(6-methylpyridin-2-yl)-5,6-dihydro-4H-pyrrolo[1,2-b]pyrazol-3-yl)-1H-benzo[d]imidazol-1-yl)propan-1-ol
1-methyl-6-(2-pyridin-2-yl-5,6-dihydro-4H-pyrrolo[1,2-b]pyrazol-3-yl)-1Hbenzoimidazole
6-[2-(6-methyl-pyridin-2-yl)-5,6-dihydro-4H-pyrrolo[1,2-b]pyrazol-3-yl]-1Hbenzoimidazole 6-[2-(6-methyl-pyridin-2-yl)-5,6-dihydro-4H-pyrrolo[1,2-b]pyrazol-3-yl]-1-(3-piperidin-1-yl-propyl)-1H-benzoimidazole 6-(2-(pyridin-2-yl)-5,6-dihydro-4H-pyrrolo[1,2-b]pyrazol-3-yl)-1-(3-(pyrrolidin-1-yl)propyl)-1H-benzo[d]imidazole 4-(3-(6-(2-(6-methylpyridin-2-yl)-5,6-dihydro-4H-pyrrolo[1,2-b]pyrazol-3-yl)-1H-benzo[d]imidazol-1-yl)propyl)morpholine 6-[2-(6-methyl-pyridin-2-yl)-5,6-dihydro-4H-pyrrolo[1,2-b]pyrazol-3-yl]-1-(3-piperidin-1-yl-propyl)-1H-benzoimidazole 4-(3-(6-(2-(6-methylpyridin-2-yl)-5,6-dihydro-4H-pyrrolo[1,2-b]pyrazol-3-yl)-1H-benzo[d]imidazol-1-yl)propyl)morpholine 6-[2-(6-methyl-pyridin-2-yl)-5,6-dihydro-4H-pyrrolo[1,2-b]pyrazol-3-yl]-1Hbenzoimidazole 1-methyl-5-(2-(6-methylpyridin-2-yl)-5,6-dihydro-4H-pyrrolo[1,2-b]pyrazol-3-yl)-1H-benzo[d]imidazole N,N-dimethyl-3-(5-(2-(pyridin-2-yl)-5,6-dihydro-4H-pyrrolo[1,2-b]pyrazol-3-yl)-1H-benzo[d]imidazol-1-yl)propan-1-amine 6-(2-(pyridin-2-yl)-5,6-dihydro-4H-pyrrolo[1,2-b]pyrazol-3-yl)-1-(3-(pyrrolidin-1-yl)propyl)-1H-benzo[d]imidazole dimethyl-(3-{6-[2-(6-methyl-pyridin-2-yl)-5,6-dihydro-4H-pyrrolo[1,2-b]pyrazol-3-yl]-benzoimidazol-1-yl}-propyl)-amine 4-(3-(6-(2-(6-methylpyridin-2-yl)-5,6-dihydro-4H-pyrrolo[1,2-b]pyrazol-3-yl)-1H-benzo[d]imidazol-1-yl)propyl)morpholine 3-(benzo[d][1,3]dioxol-5-yl)-2-(pyridin-2-yl)-6,7-dihydro-5H-pyrrolo[1,2-a]imidazole 6-bromo-4-(2-(6-methylpyridin-2-yl)-5,6-dihydro-4H-pyrrolo[1,2-b]pyrazol-3-yl)quinoline 3-hydroxy-N-(4-(2-(pyridin-2-yl)-5,6-dihydro-4H-pyrrolo[1,2-b]pyrazol-3-yl)quinolin-7-yl)propanamide 4-(2-(pyridin-2-yl)-5,6-dihydro-4H-pyrrolo[1,2-b]pyrazol-3-yl)-2-(pyrrolidin-1-yl)quinoline 4-[4-(2-pyridin-2-yl-5,6-dihydro-4H-pyrrolo[1,2-b]pyrazol-3-yl)-quinolin-7-yloxy]-benzonitrile 1-(3-(dimethylamino)propyl)-3-(4-(2-(pyridin-2-yl)-5,6-dihydro-4H-pyrrolo[1,2-b]pyrazol-3-yl)quinolin-7-yl)urea 4-[4-(2-pyridin-2-yl-5,6-dihydro-4H-pyrrolo[1,2-b]pyrazol-3-yl)-quinolin-7-yloxy]-benzamide methyl 4-(2-(pyridin-2-yl)-5,6-dihydro-4H-pyrrolo[1,2-b]pyrazol-3-yl)quinolin-7-ylcarbamate 6,8-dimethoxy-4-(2-(6-methylpyridin-2-yl)-5,6-dihydro-4H-pyrrolo[1,2-b]pyrazol-3-yl)quinoline dimethyl-{5-[4-(2-pyridin-2-yl-5,6-dihydro-4H-pyrrolo[1,2-b]pyrazol-3-yl)-quinolin-7-yloxy]-pentyl}-amine 8-fluoro-4-(2-(6-methylpyridin-2-yl)-5,6-dihydro-4H-pyrrolo[1,2-b]pyrazol-3-yl)quinoline 4-(2-(6-methylpyridin-2-yl)-5,6-dihydro-4H-pyrrolo[1,2-b]pyrazol-3-yl)-6-(trifluoromethoxy)quinoline dimethyl-{4-[4-(2-pyridin-2-yl-5,6-dihydro-4H-pyrrolo[1,2-b]pyrazol-3-yl)-quinolin-7-yloxy]-benzyl}-amine 7-ethoxy-4-(2-(6-methylpyridin-2-yl)-5,6-dihydro-4H-pyrrolo[1,2-b]pyrazol-3-yl)quinoline 2-hydroxyethyl 4-(2-(pyridin-2-yl)-5,6-dihydro-4H-pyrrolo[1,2-b]pyrazol-3-yl)quinolin-7-ylcarbamate ethyl-methyl-{2-[4-(2-pyridin-2-yl-5,6-dihydro-4H-pyrrolo[1,2-b]pyrazol-3-yl)-quinolin-7-yloxy]-ethyl}-amine 4-(2-(6-ethylpyridin-2-yl)-5,6-dihydro-4H-pyrrolo[1,2-b]pyrazol-3-yl)quinoline 2-(dimethylamino)-N-(4-(2-(pyridin-2-yl)-5,6-dihydro-4H-pyrrolo[1,2-b]pyrazol-3-yl)quinolin-7-yl)acetamide 2-(4-(2-(pyridin-2-yl)-5,6-dihydro-4H-pyrrolo[1,2-b]pyrazol-3-yl)quinolin-7-yloxy)ethanol 3-methoxy-N-(4-(2-(pyridin-2-yl)-5,6-dihydro-4H-pyrrolo[1,2-b]pyrazol-3-yl)quinolin-7-yl)propanamide 1-(2-(dimethylamino)ethyl)-3-(4-(2-(pyridin-2-yl)-5,6-dihydro-4H-pyrrolo[1,2-b]pyrazol-3-yl)quinolin-7-yl)urea N-(4-(2-(pyridin-2-yl)-5,6-dihydro-4H-pyrrolo[1,2-b]pyrazol-3-yl)quinolin-7-yl)acetamide 2-(ethylthio)-4-(2-(pyridin-2-yl)-5,6-dihydro-4H-pyrrolo[,2-b]pyrazol-3-yl)quinoline 7-[3-(4-methyl-piperazin-1-yl)-propoxy]-4-(2-pyridin-2-yl-5,6-dihydro-4H-pyrrolo[1,2-b]pyrazol-3-yl)-quinoline 4-(2-(pyridin-2-yl)-5,6-dihydro-4H-pyrrolo[1,2-b]pyrazol-3-yl)quinolin-7-amine 7-chloro-4-(2-(pyridin-2-yl)-5,6-dihydro-4H-pyrrolo[1,2-b]pyrazol-3-yl)quinoline 7-chloro-4-(2-(6-methylpyridin-2-yl)-5,6-dihydro-4H-pyrrolo[1,2-b]pyrazol-3-yl)quinoline N-(2-(dimethylamino)ethyl)-4-(2-(6-methylpyridin-2-yl)-5,6-dihydro-4H-pyrrolo[1,2-b]pyrazol-3-yl)quinoline-6-carboxamide 7-(ethylsulfonyl)-4-(2-(pyridin-2-yl)-5,6-dihydro-4H-pyrrolo[1,2-b]pyrazol-3-yl)quinoline 4-(2-(5-fluoropyridin-2-yl)-5,6-dihydro-4H-pyrrolo[1,2-b]pyrazol-3-yl)quinoline 7-(2-chloro-ethoxy)-4-(2-pyridin-2-yl-5,6-dihydro-4H-pyrrolo[1,2-b]pyrazol-3-yl)-quinoline N,N-dimethyl-4-[4-(2-pyridin-2-yl-5,6-dihydro-4H-pyrrolo[1,2-b]pyrazol-3-yl)-quinolin-7-yloxy]-benzamide 4-(2-(6-methylpyridin-2-yl)-5,6-dihydro-4H-pyrrolo[1,2-b]pyrazol-3-yl)quinoline 7-(ethylthio)-4-(2-(pyridin-2-yl)-5,6-dihydro-4H-pyrrolo[1,2-b]pyrazol-3-yl)quinoline 4-(2-(pyridin-2-yl)-5,6-dihydro-4H-pyrrolo[1,2-b]pyrazol-3-yl)quinoline 4-[4-(2-pyridin-2-yl-5,6-dihydro-4H-pyrrolo[1,2-b]pyrazol-3-yl)-quinolin-7-yloxy]-benzoic acid 4-(2-pyridin-2-yl-5,6-dihydro-4H-pyrrolo[1,2-b]pyrazol-3-yl)-quinolin-7-ol 2-chloro-4-(2-(pyridin-2-yl)-5,6-dihydro-4H-pyrrolo[1,2-b]pyrazol-3-yl)quinoline 7-[3-(1-methyl-pyrrolidin-2-yl)-propoxy]-4-(2-pyridin-2-yl-5,6-dihydro-4H-pyrrolo[1,2-b]pyrazol-3-yl)-quinoline methyl 4-(2-(6-methylpyridin-2-yl)-5,6-dihydro-4H-pyrrolo[1,2-b]pyrazol-3-yl)quinoline-6-carboxylate 4-(2-pyridin-2-yl-5,6-dihydro-4H-pyrrolo[1,2-b]pyrazol-3-yl)-7-(tetrahydro-furan-2-ylmethoxy)-quinoline 7-[2-(4-methyl-piperazin-1-yl)-ethoxy]-4-(2-pyridin-2-yl-5,6-dihydro-4H-pyrrolo[1,2-b]pyrazol-3-yl)-quinoline

[4-(2-pyridin-2-yl-5,6-dihydro-4H-pyrrolo[1,2-b]pyrazol-3-yl)-quinolin-7-yloxy]-acetic acid ethyl ester 2-methoxy-4-(2-(pyridin-2-yl)-5,6-dihydro-4H-pyrrolo[1,2-b]pyrazol-3-yl)quinoline dimethyl-{2-[4-(2-pyridin-2-yl-5,6-dihydro-4H-pyrrolo[1,2-b]pyrazol-3-yl)-quinolin-7-yloxy]-ethyl}-amine 4-(2-(6-isopropylpyridin-2-yl)-5,6-dihydro-4H-pyrrolo[1,2-b]pyrazol-3-yl)quinoline 4-{[4-(5,6-Dimethyl-2-pyridin-2-yl-pyridin-3-yl)oxypyridin-2-yl]amino}-N,N-dimethyl-benzamide 4-(5,6-Dimethyl-2-pyridin-2-yl-pyridin-3-yl)oxy-N-(3-methoxyphenyl)pyridin-2-amine 4-(5,6-Dimethyl-2-pyridin-2-yl-pyridin-3-yl)oxy-N-(2-morpholin-4-ylphenyl)pyridin-2-amine 4-(5,6-Dimethyl-2-pyridin-2-yl-pyridin-3-yl)oxy-N-(2-methoxyphenyl)pyridin-2-amine 4-{[4-(5,6-Dimethyl-2-pyridin-2-yl-pyridin-3-yl)oxypyridin-2-yl]amino}benzenesulfonamide 4-(2-Methylpyridin-3-yl)oxy-N-(3,4,5-trimethoxyphenyl)-pyridin-2-amine
4-(2-Methylpyridin-3-yl)oxy-N-(3,4,5-trimethoxyphenyl)-pyridin-2-amine
4-(5,6-Dimethyl-2-pyridin-2-yl-pyridin-3-yl)oxy-N-(4-methoxyphenyl)pyridin-2-amine
4-(5,6-Dimethyl-2-pyridin-2-yl-pyridin-3-yl)oxy-N-(2-methoxyphenyl)pyridin-2-amine
4-(2,6-Dimethylpyridin-3-yl)oxy-N-(3,4,5-trimethoxyphenyl)-pyridin-2-amine
4-({4-[(2,6-Dimethylpyridin-3-yl)oxy]pyridin-2-yl}amino)benzenesulfonamide
4-(5,6-Dimethyl-2-pyridin-2-yl-pyridin-3-yl)oxy-N-(4-morpholin-4-ylphenyl)pyridin-2-amine
4-[5,6-dimethyl-2,2'-bipyridin-3-yl)oxy]-N-(3,4,5-trimethyloxyphenyl)pyridine-2-amine
4-(5,6-Dimethyl-2-pyridin-2-yl-pyridin-3-yl)oxy-N-(4-morpholin-4-ylphenyl)pyridin-2-amine
4-Pyridin-3-yloxy-N-(3,4,5-trimethoxyphenyl)pyridin-2-amine
4-(6-Methyl-2-pyridin-2-yl-pyridin-3-yl)oxy-N-(3,4,5-trimethoxyphenyl)pyridin-2-amine
4-{([4-(5,6-Dimethyl-2-pyridin-2-yl-pyridin-3-yl)oxypyridin-2-yl]amino}benzenesulfonamide
4-(2,6-Dimethylpyridin-3-yl)oxy-N-(3,4,5-trimethoxyphenyl)-pyridin-2-amine
4-(6-Methylpyridin-3-yl)oxy-N-(3,4,5-trimethoxyphenyl)-pyridin-2-amine
4-(5,6-Dimethyl-2-pyridin-2-yl-pyridin-3-yl)oxy-N-(3-morpholin-4-ylphenyl)pyridin-2-amine
4-({4-[(2,6-Dimethylpyridin-3-yl)oxy]pyridin-2-yl}amino)benzenesulfonamide
4-(5,6-Dimethyl-2-pyridin-2-yl-pyridin-3-yl)oxy-N-(4-methoxyphenyl)pyridin-2-amine
4-(5,6-Dimethyl-2-pyridin-2-yl-pyridin-3-yl)oxy-N-(4-fluorophenyl)pyridin-2-amine
4-(6-Methylpyridin-3-yl)oxy-N-(3,4,5-trimethoxyphenyl)-pyridin-2-amine
4-(6-Methyl-2-pyridin-2-yl-pyridin-3-yl)oxy-N-(3,4,5-trimethoxyphenyl)pyridin-2-amine
5-(6-Ethoxy-[1,5]naphthyridin-2-yl)-4-pyridin-2-yl-thiazol-2-ylamine
4-(3-chlorophenyl)-5-(1,5-naphthyridin-2-yl)thiazol-2-amine
4-(4-fluorophenyl)-5-(1,5-naphthyridin-2-yl)thiazol-2-amine
5-(6-Ethoxy-[1,5]naphthyridin-2-yl)-4-pyridin-2-yl-thiazol-2-ylamine
4-(6-Methyl-pyridin-2-yl)-5-[1,5]naphthyridin-2-yl-thiazol-2-ylamine
5-(1,5-naphthyridin-2-yl)-4-(pyridin-2-yl)thiazol-2-amine
4-(3-chlorophenyl)-5-(1,5-naphthyridin-2-yl)thiazol-2-amine
4-(4-fluorophenyl)-5-(1,5-naphthyridin-2-yl)thiazol-2-amine
4-(3-chlorophenyl)-5-(1,5-naphthyridin-2-yl)thiazol-2-amine
5-(6-methyl-1,5-naphthyridin-4-yl)-4-(pyridin-2-yl)thiazol-2-amine
5-[1,8]Naphthyridin-4-yl-4-pyridin-2-yl-thiazol-2-ylamine
5-(1,5-naphthyridin-2-yl)-4-(pyridin-2-yl)thiazol-2-amine
5-(8-Methyl-[1,5]naphthyridin-2-yl)-4-pyridin-2-yl-thiazol-2-ylamine
5-(6-methyl-1,5-naphthyridin-4-yl)-4-(pyridin-2-yl)thiazol-2-amine
4-(3-methylpyridin-2-yl)-5-(1,5-naphthyridin-2-yl)thiazol-2-amine
4-(3-chlorophenyl)-5-(1,5-naphthyridin-2-yl)thiazol-2-amine
5-[1,8]Naphthyridin-4-yl-4-pyridin-2-yl-thiazol-2-ylamine
4-[5-Benzo[1,3]dioxol-5-yl-4-(6-methyl-pyridin-2-yl)-1H-imidazol-2-yl]-bicylo[2.2.2]octane-1-carboxylic acid amide
4-[5-Benzo[1,3]dioxol-5-yl-4-(6-ethyl-pyridin-2-yl)-1H-imidazol-2-yl]-bicylo[2.2.2.]octane-1-carboxylic acid amide
4-[5-Benzo[1,3]dioxol-5-yl-4-(6-methyl-pyridin-2-yl)-1H-imidazol-2-yl]-bicylo[2.2.2.]octane-1-carboxylic acid
4-[5-Benzo[1,3]dioxol-5-yl-4-(6-ethyl-pyridin-2-yl)-1H-imidazol-2-yl]-bicylo[2.2.2]octane-1-carboxylic acid Although the $IC_{50}$ values for these compounds are generally in the low nanomolar range, these compounds have been shown to be effective against TGF-β-induced epithelial-mesenchymal-transitions, tumor-cell invasions and metastasis at concentrations of 1-2 micromolar.

Illustrative, non-limiting examples of the possible points of attachment of the ALK5 inhibitors to the monosaccharides and oligosaccharides oin accordance with the present invention are suggested below by an asterisk:

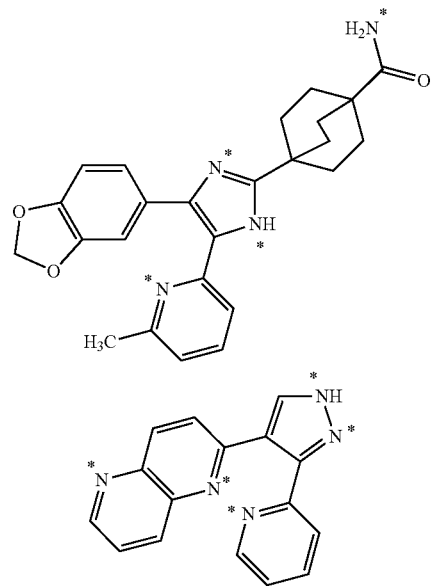

We expect that several advantages will be demonstrated by selectively targeting Muc4 tumor cells with our proprietary TGF-β ALK5 inhibitor-glycoconjugates when administered to patients. First, the TGF-β ALK5 inhibitor-glycoconjugates provide specific modulation of Muc4 overexpression and glycosylation of Muc4 on tumors. This will potentially reduce transformation and motility of mesenchymal cells from the primary breast tumors to different metastatic sites. Secondly, the small molecule nature of our TGF-β ALK5 inhibitor-glycoconjugates overcomes deficiencies found with other delivery mechanisms such as monoclonal antibodies, cationic liposomes, microspheres and lectins. Monoclonal antibodies (10-12 nm), cationic liposomes (105-267 nm) and microspheres (>>200 nm) are too large to penetrate the rigid carbohydrate tentacles on the remodeled Muc4-containing cells; whereas our TGF-β ALK5 inhibitor-glycoconjugates are much smaller (~2 nm) and have more favorable hydrodynamic properties for reaching the cell surface. Unlike lectins having low potency for cell surfaces, the specificity of our TGF-β ALK5 inhibitor-glycoconjugates are not dependent upon specific carbohydrate remodeling of galactose and sialic acids containing sLe$^x$ and sLe$^a$ that are subject to genetic polymorphism Unless otherwise specifically identified or claimed for preferred embodiments, the following general definitions are used in accordance with the present invention.

In accordance with the present invention, the term "pharmacologically active residue" or like term refers to that portion of the conjugated inhibitor which, upon release from the saccharide conjugate, forms a compound that exhibits the pharmacological activity of the inhibitor. It will become apparent to those skilled in the art that the inhibitor residue covalently bound to the saccharide will contain fewer atoms in its structure than the pharmacologically active inhibitor that is released upon liberation from the saccharide.

In accordance with the present invention, the term "targetable" or "to target" refers to the recognition of a target and delivery of a drug to that target by the glycoconjugates; however, no internalization of the drug or drug conjugate is inferred. "Targeting" in accordance with the present invention includes, without limitation surrounding tumors or tumor cells such that the glycoconjugates accumulate within the immediate vicinity of the tumor cells. Internalization of the inhibitor is considered a separate event, and likely occurs upon release of the inhibitor from the saccharide. In accordance with the present invention, the term "selectively target" refers to selective preference of one cell type over another. In accordance with the present invention, the term "modulate" refers to a change in the parameter measured, such that modulate can mean either an increase or decrease. In accordance with the present invention, the term alkyl or alkylene refers to a branched or straight chain acyclic group comprising one to about ten carbon atoms. In accordance with the present invention, the term lower alkyl refers to a branched or straight chain acyclic alkyl group comprising 1 to about 5 carbon atoms. In accordance with the present invention, lower alkyls include methyl, ethyl, propyl, isopropyl and the like. In accordance with the present invention, cycloalkyl refers to a saturated or unsaturated cyclic hydrocarbon comprising from about 3 to about 8 carbon atoms. In accordance with the present invention, cycloalkyl groups include cyclopropyl, cyclobutyl, cyclopentyl, cyclohexyl, cyclohexenyl, cycloheptyl and the like.

In accordance with the present invention, the term aryl refers to a unsubstituted or substituted monocyclic, bicyclic, carbocyclic or heterocyclic ring system comprising one or two aromatic rings. In accordance with the present invention, aryl groups include phenyl, pyridyl, napthyl, quinoyl, tetrahydronaphthyl, furanyl, indanyl, indenyl, indoyl, and the like.

In accordance with the present invention, the term arylalkyl refers to an aryl radical, attached to an alkyl radical, and the term aminoalkyl refers to an amine radical attached to an alkyl radical.

Therapeutic drug oligosaccharide conjugates are described in U.S. Pat. Nos. 6,699,848 and 7,119,079, which are hereby incorporated by reference.

In one embodiment tumor-targeted glycoconjugates useful in accordance with the present invention comprise compounds having the formula

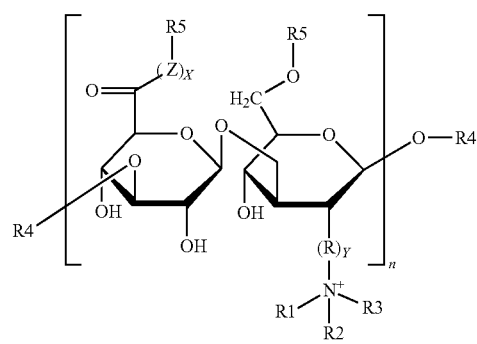

where R is an alkyl or alkylene, Y=0 or 1, $R_1$, $R_2$ and $R_3$ are independently hydrogen, alkyl, aryl, aralkyl and cycloalkyl, $R_4$ is independently hydrogen or lower alkyl, n is an integer from 1 to about 6, Z is a linker, X is 0 or 1, $R_5$ is hydrogen or a pharmacologically active residue of an ALK5 inhibitor, with the proviso said compound contains at least one pharmacologically active residue of an ALK5 inhibitor, and pharmaceutically acceptable salts thereof. In accordance with the present invention, these tumor-targeted glycoconjugates selectively bind to Muc4 mucins on tumor cells. In a preferred embodiment of the present invention, Z is an acid-labile linker.

In accordance with the present invention, R is an alkyl chain containing only carbon atoms or a heteroalkyl containing carbon, nitrogen and oxygen atoms. Examples of heteroalkyls include —NHC(O)CH$_2$— and —NHC(O)CH$_2$CH$_2$—. In accordance with the present invention, R is an alkyl having from 1 to about 6 carbon atoms. In a preferred embodiment of the present invention, R is a lower alkyl having from 1 to about 3 carbon atoms. In accordance with a more preferred embodiment of the present invention, R is —CH$_2$ or —CH$_2$CH$_2$—. In accordance with the present invention, Y is either 0 or 1. In accordance with a preferred embodiment of the present invention, Y is 0.

In accordance with the present invention, $R_1$, $R_2$ and $R_3$ are independently hydrogen, alkyl, aryl and cycloalkyl. Preferred alkyls for $R_1$, $R_2$ and $R_3$ are those having from 1 to about 6 carbon atoms including but not limited to methyl, ethyl, propyl, butyl, isobutyl, pentyl and hexyl. More preferably the alkyls contain from 1 to about 3 carbon atoms. In accordance with the present invention, $R_1$, $R_2$ and $R_3$ are each methyl or ethyl. Preferred aryls are those including but not limited to phenyl and pyridinyl, while a preferred aralkyl is benzyl. Preferred cycloalkyls are those having from about 3 to about 6 carbon atoms including but not limited to cyclopropyl, cyclobutyl, cyclopentyl, and cyclohexyl.

In accordance with the present invention, $R_4$ is independently hydrogen or lower alkyl. When $R_4$ is an alkyl, $R_4$ is methyl, ethyl or propyl. Preferably, $R_4$ is hydrogen.

In accordance with this embodiment of the present invention, the oligosaccharides include multiple glycosides such that n is an integer from about 1 to about 6. In one preferred embodiment of the present invention, the conjugates include an oligosaccharide where n is an integer from 1 to about 3. In a more preferred embodiment, the conjugates include an oligosaccharide where n is an integer 1

In another embodiment tumor-targeted glycoconjugates useful in accordance with the present invention comprise compounds having the formula

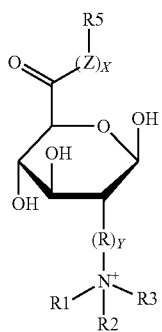

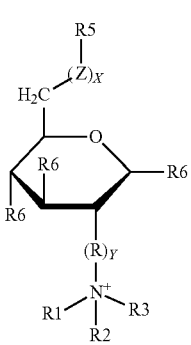

where R is an alkyl or alkylene, Y=0 or 1, $R_1$, $R_2$ and $R_3$ are independently hydrogen, alkyl, aryl, aralkyl and cycloalkyl, $R_4$ is independently hydrogen or lower alkyl, n is an integer from 1 to about 6, Z is a linker, X is 0 or 1, $R_5$ is hydrogen or a pharmacologically active residue of an ALK5 inhibitor, with the proviso said compound contains at least one pharmacologically active residue of an ALK5 inhibitor, and pharmaceutically acceptable salts thereof.

In a preferred embodiment of the present invention, inhibitors are conjugated to 2-amino-D-glucuronic acid (CAS No. 50767-83-4).

In another embodiment tumor-targeted glycoconjugates useful in accordance with the present invention comprise compounds having the formula

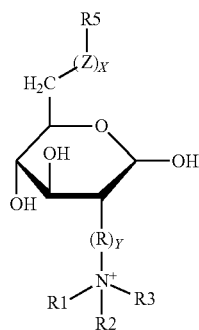

where R is an alkyl, Y=0 or 1, $R_1$, $R_2$ and $R_3$ are independently hydrogen, alkyl, aryl, aralkyl and cycloalkyl, $R_4$ is independently hydrogen or lower alkyl, n is an integer from 1 to about 6, Z is a linker, X is 0 or 1, $R_5$ is hydrogen or a pharmacologically active residue of an ALK5 inhibitor, with the proviso said compound contains at least one pharmacologically active residue of an ALK5 inhibitor, and pharmaceutically acceptable salts thereof.

In accordance with yet another embodiment of the invention, tumor-targeted conjugates comprise compounds having the formula where $R_6$ is independently hydrogen, lower alkyl having from one to about 5 carbon atoms or an alkoxy group having from 1 to about 3 carbon atoms, and the other substituents are the same as those described immediately above.

In accordance with the present invention, Z is a hydrazone-based linker, a carbohydrazide-based linker, a sulfohydrazide-based linker, or a dihydrazide-based linker. Illustrative glycoconjugate precursors having dihydrazide linkers include compounds having the formulas

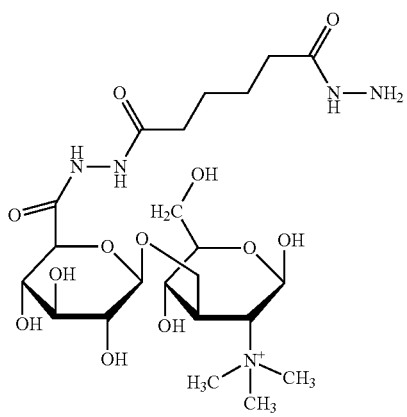

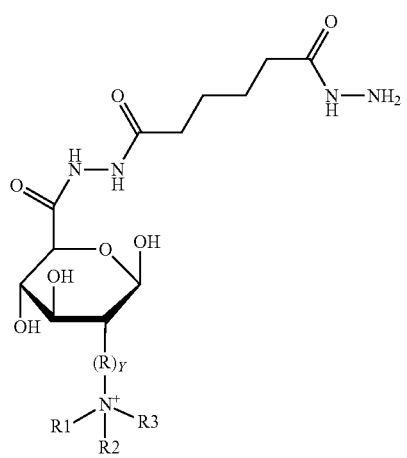

-continued

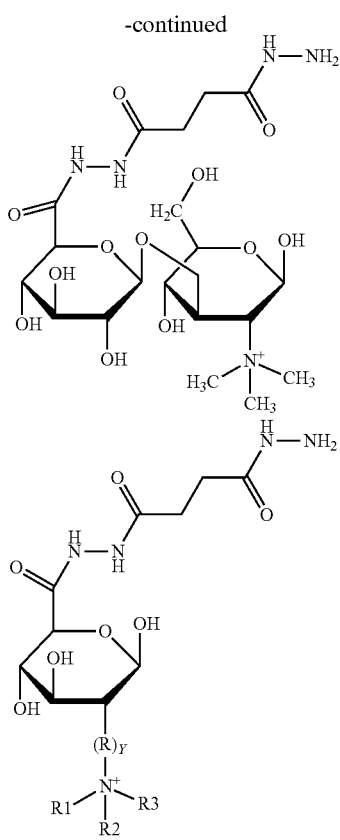

It will be understood by those skilled in the art that the certain acid-labile linkers are more hydrolytically stable than ester bond linkages that are subject to hydrolysis by esterases in the plasma. That is, inhibitor glycoconjugates having acid-labile linkers can have different rates of hydrolysis as a function of pH, and can release the pharmacologically active inhibitors partially or exclusively by acid hydrolysis and enzyme (e.g. esterase) hydrolysis. The extent and relative rates of hydrolysis for the two types of inhibitor release in plasma or in vitro media are easily determined, and can be used to select the most suitable acid-labile linkers (See for example Luo Y et al. Biomacromolecules 1, 208-218 (2000)). In a preferred embodiment of the present invention, the extent or rate of release of the pharmacologically active ALK5 inhibitor will be predominantly by acid hydrolysis rather then enzymatic hydrolysis. In a most preferred embodiment, the extent or release of the pharmacologically active ALK5 inhibitor will be essentially by acid hydrolysis or be essentially free of enzymatic hydrolysis. Examples of acid-labile linkers suitable for use in the present invention include, but are not limited to, those described in U.S. Pat. Nos. 4,542,225; 4,569,789; 4,618,492; 4,952,394; 5,708,146 and 7,585,491 which are hereby incorporated by reference in their entirety.

The extent of tumor targeting and cellular uptake of the water-soluble low molecular weight oligosaccharide ALK5 inhibitor-conjugates of the present invention is determined by a number of conventional techniques described in the scientific literature, including immunofluorescent staining (e.g. FITC or Texas Red) followed by confocal microscopic imaging and flow cytometry/fluorescence activated cell sorting (FACS) using fluorescein labeled conjugates. The effects of our proprietary water-soluble low molecular weight oligosaccharide ALK5 inhibitor-conjugates on Muc4 expression, TGF-β induced ALK5/Smad2 EMT signaling, metastatic potential and in vivo tumorigenicity can easily be determined by a number of conventional techniques described in the scientific literature.

Determining the dose and the amount of ALK5 inhibitor-conjugates effective reducing aberrant Muc4 expression and tumorigenicity in accordance with the present invention will be readily apparent to those skilled in the art. In accordance with one aspect of the present invention, a method for treating a subject having cancer comprises administering to the subject a water-soluble low molecular weight oligosaccharide ALK5 inhibitor-conjugate in an amount effective in modulating one or more of Muc4 expression, TGF-β induced ALK5/Smad2 EMT signaling, metastatic potential and in vivo tumorigenicity.

In accordance with a preferred embodiment of the present invention, the tumor-targeted inhibitor glycoconjugates are administered parenterally, and the preferred route of parenteral administration is intravenous. In accordance with standard practice, tumor-targeted inhibitor glycoconjugates are prepared in an admixture with a pharmaceutically acceptable salt or carrier. The term "carrier" refers to diluents, excipients and the like for use in preparing admixtures of a pharmaceutical composition. Pharmaceutically acceptable carriers include but are not limited to sterile water, saline, buffered saline, dextrose solution, preferably such physiologically compatible buffers as Hank's or Ringer's solution, physiological saline, a mixture consisting of saline and glucose, and heparinized sodium-citrate-citric acid-dextrose solution and the like. As used herein, the term "pharmaceutically acceptable" means approved by a regulatory agency of the Federal or a state government or listed in the U.S. Pharmacopeia or other generally recognized pharmacopeia for use in animals, and more particularly in humans.

The present invention has been described in detail using specific examples to illustrate the preferred embodiments of the invention; however, it will be obvious to those skilled in the art that various modifications thereto can be made without departing from the spirit and scope thereof.

I claim:

1. A method for treating a subject having breast cancer, ovarian cancer, or pancreatic cancer in need of therapy thereof comprising administering to the subject a compound in an amount effective in reducing the migration or metastatic dissemination of mesenchymal tumor cells, said compound having the formula

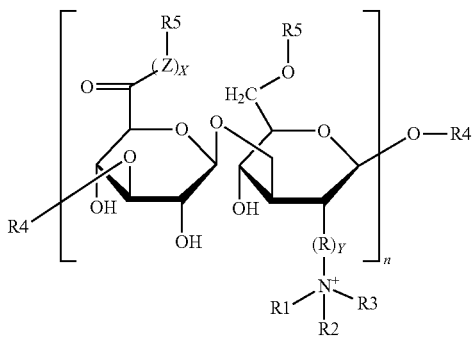

or a compound having the formula

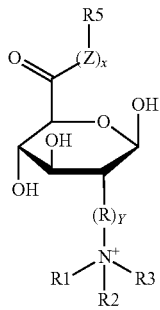

or a compound having the formula

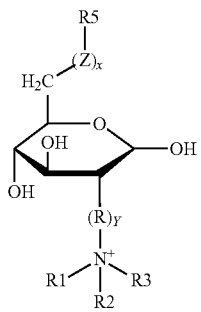

where R is an alkyl, Y=0 or 1, R1, R2 and R3 are independently hydrogen, alkyl, aryl, aralkyl or cycloalkyl, R4 is independently hydrogen or lower alkyl, n is an integer from 1 to 6, Z is a linker, X is 0 or 1, R5 is hydrogen or a pharmacologically active residue of an ALK5 inhibitor, with the proviso said compound contains at least one pharmacologically active residue of an ALK5 inhibitor; and pharmaceutically acceptable salts thereof, in combination with pharmaceutically acceptable carriers and diluents.

2. A method for treating a subject having a breast cancer, ovarian cancer, or pancreatic cancer in need of therapy thereof comprising administering to the subject a TGF-β ALK5 inhibitor-glycoconjugate in an amount effective in reducing the migration, extravasation or metastatic dissemination of mesenchymal tumor cells; wherein said TGF-β ALK5 inhibitor-glycoconjugate is a compound having the formula

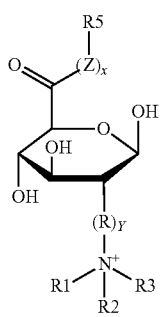

or a compound having the formula

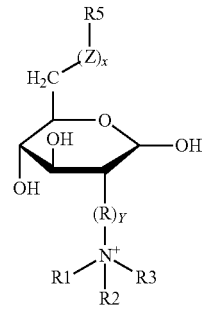

where R is an alkyl, Y=0 or 1, R1, R2 and R3 are independently hydrogen, alkyl, aryl, aralkyl or cycloalkyl, R4 is independently hydrogen or lower alkyl, n is an integer from 1 to 6, Z is a linker, X is 0 or 1, R5 is a pharmacologically active residue of an ALK5 inhibitor; and pharmaceutically acceptable salts thereof, in combination with pharmaceutically acceptable carriers and diluents.

3. A method for treating a subject having a breast cancer, ovarian cancer, or pancreatic cancer in need of therapy thereof comprising administering to the subject a compound in an amount effective in reducing the migration or metastatic dissemination of mesenchymal tumor cells, said compound having the formula

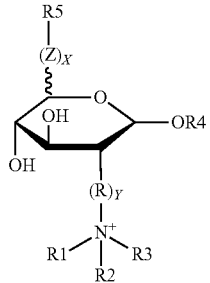

where R is an alkyl, Y=0 or 1, R1, R2 and R3 are independently hydrogen, alkyl, aryl, aralkyl or cycloalkyl, R4 is hydrogen or lower alkyl, Z is a linker, X is 0 or 1, R5 is a pharmacologically active residue of an ALK5 inhibitor and pharmaceutically acceptable salts thereof, in combination with pharmaceutically acceptable carriers and diluents.

4. The method of claim 3 wherein R5 of the compound is a residue of formula

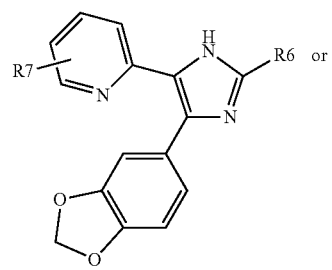

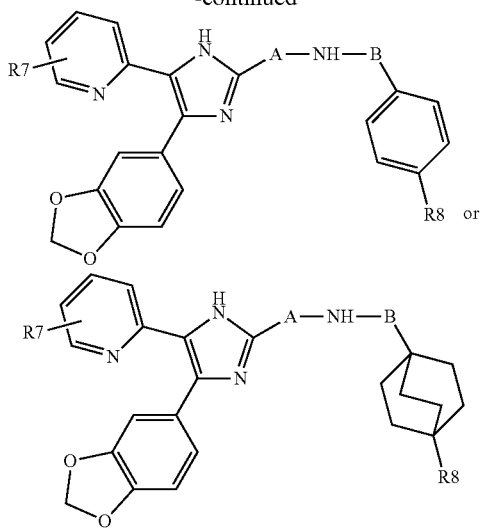

where R6 is hydrogen or a lower alkyl having from 1 to 5 carbon atoms, R7 is hydrogen or lower alkyl having from 1 to 5 carbon atoms and R8 is an amide, nitrile, alkynyl having from 1 to 3 carbon atoms, carboxyl or alkanol group having from 1 to 5 carbon atoms, A is a direct bond or an alkyl having from 1 to 5 carbon atoms and B is a direct bond or an alkyl having from 1 to 5 carbon atoms.

5. The method of claim 3 wherein R5 of the compound is a residue of one of the following ALK5 inhibitors:

4-(4-(2,3-dihydrobenzo[b][1,4]dioxin-6-yl)-5-(pyridin-2-yl)-1H-imidazol-2-yl)benzamide;
3-((4-(benzo[d][1,3]dioxol-5-yl)-5-(6-methylpyridin-2-yl)-1H-imidazol-2-yl)methylamino)benzamide;
4-((4-(benzo[d][1,3]dioxol-5-yl)-5-(6-ethylpyridin-2-yl)-1H-imidazol-2-yl)methylamino)benzamide;
4-(4-(benzo[d][1,3]dioxol-5-yl)-5-(pyridin-2-yl)-1H-imidazol-2-yl)benzamide;
4-((4-(3a,4-dihydrobenzo[d][1,3]dioxol-5-yl)-5-(6-ethylpyridin-2-yl)-1H-imidazol-2-yl)methylamino)benzamide;
4-(4-(3a,4-dihydrobenzo[d][1,3]dioxol-5-yl)-5-(pyridin-2-yl)-1H-imidazol-2-yl)benzoic acid;
4-(4-(benzo[d][1,3]dioxol-5-yl)-5-(pyridin-2-yl)-1H-imidazol-2-yl)benzamide;
4-((4-(benzo[d][1,3]dioxol-5-yl)-5-(6-methylpyridin-2-yl)-1H-imidazol-2-yl)methylamino)benzamide;
4-(4-(benzo[d][1,3]dioxol-5-yl)-5-(pyridin-2-yl)-1H-imidazol-2-yl)benzoic acid;
3-((4-(benzo[d][1,3]dioxol-5-yl)-5-(6-ethylpyridin-2-yl)-1H-imidazol-2-yl)methylamino)benzamide;
3-((5-(6-methylpyridin-2-yl)-4-(quinoxalin-6-yl)-1H-imidazol-2-yl)methyl)benzamide;
4-((5-(6-ethylpyridin-2-yl)-4-(quinoxalin-6-yl)-1H-imidazol-2-1)methylamino)benzamide;
4-((5-(6-methylpyridin-2-yl)-4-(1,4,4a,8a-tetrahydroquinoxalin-6-yl)-1H-imidazol-2-yl)methylamino)benzamide;
4-((5-(6-ethylpyridin-2-yl)-4-(quinoxalin-6-yl)-1H-imidazol-2-1)methylamino)benzamide;
3-((5-(6-ethylpyridin-2-yl)-4-(quinoxalin-6-yl)-1H-imidazol-2-1)methylamino)benzamide;
3-((5-(6-methylpyridin-2-yl)-4-(quinoxalin-6-yl)-1H-imidazol-2-yl)methyl)benzamide;
4-((5-(6-ethylpyridin-2-yl)-4-(1,4,4a,8a-tetrahydroquinoxalin-6-yl)-1H-imidazol-2-yl)methylamino)benzamide;
3-((5-(6-methylpyridin-2-yl)-4-(1,5-naphthyridin-2-yl)-1H-pyrazol-1-yl)methyl)benzamide;
3-((3-(6-methylpyridin-2-yl)-4-(1,5-naphthyridin-2-yl)-1H-pyrazol-1-yl)methyl)benzamide;
3-((3-(6-methylpyridin-2-yl)-4-(quinolin-6-yl)-1H-pyrazol-1-yl)methyl)benzamide;
3-((4-(6-methylpyridin-2-yl)-4-(quinolin-6-yl)-1H-pyrazol-1-yl)methyl)benzamide;
4-[5-benzo[1,3]dioxol-5-yl-4-(6-methyl-pyridin-2-yl)-1H-imidazol-2-yl]-bicylo[2.2.2.]octane-1-carboxylic acid amide;
4-[5-benzo[1,3]dioxol-5-yl-4-(6-ethyl-pyridin-2-yl)-1H-imidazol-2-yl]-bicylo[2.2.2]octane-1-carboxylic acid amide;
4-[5-benzo[1,3]dioxol-5-yl-4-(6-methyl-pyridin-2-yl)-1H-imidazol-2-yl]-bicylo[2.2.2.]octane-1-carboxylic acid; or
4-[5-benzo[1,3]dioxol-5-yl-4-(6-ethyl-pyridin-2-yl)-1H-imidazol-2-yl]-bicylo[2.2.2.]octane-1-carboxylic acid.

* * * * *